(12) United States Patent
Yun et al.

US011801222B2

(10) Patent No.: US 11,801,222 B2
(45) Date of Patent: Oct. 31, 2023

(54) MANUFACTURING METHOD FOR GRANULE

(71) Applicant: Korea Institute of Machinery & Materials, Daejeon (KR)

(72) Inventors: Hui Suk Yun, Changwon-si (KR); Honghyun Park, Changwon-si (KR)

(73) Assignee: KOREA INSTITUTE OF MATERIALS SCIENCE, Gyeongsangnam-Do (KR)

(*) Notice: Subject to any disclaimer, the term of this patent is extended or adjusted under 35 U.S.C. 154(b) by 0 days.

(21) Appl. No.: 16/598,299

(22) Filed: Oct. 10, 2019

(65) Prior Publication Data

US 2020/0188302 A1 Jun. 18, 2020

Related U.S. Application Data

(63) Continuation-in-part of application No. PCT/KR2018/004363, filed on Apr. 13, 2018, and a continuation-in-part of application No. PCT/KR2018/004362, filed on Apr. 13, 2018.

(30) Foreign Application Priority Data

Apr. 14, 2017 (KR) .................. 10-2017-0048463
Aug. 7, 2017 (KR) .................. 10-2017-0099806

(51) Int. Cl.
*A61K 9/16* (2006.01)
*A61L 27/12* (2006.01)
*A61L 27/42* (2006.01)

(52) U.S. Cl.
CPC ............ *A61K 9/1694* (2013.01); *A61L 27/12* (2013.01); *A61L 27/425* (2013.01)

(58) Field of Classification Search
CPC .. A61K 9/1694; A61K 9/1611; A61K 9/1652; A61L 27/12; A61L 27/425; A61L 27/56; A61L 2400/12; A61L 2400/06; A61L 2430/34; C04B 35/03; C04B 35/626; C04B 35/636; C04B 35/64
See application file for complete search history.

(56) References Cited

U.S. PATENT DOCUMENTS 3,415,493 A * 12/1968 Bates .................... B01F 27/707
366/325.4
4,032,117 A * 6/1977 Burgess ................. B01F 27/114
366/307
5,639,467 A 6/1997 Dorian et al.
7,823,809 B2 * 11/2010 Yamaguchi ........... B05B 5/0533
239/690.1
2005/0170012 A1 8/2005 Dalal et al.

FOREIGN PATENT DOCUMENTS

| KR | 20100138128 | * | 6/2004 | ............ A61L 27/10 |
|---|---|---|---|---|
| KR | 10-2010-0026910 A | | 3/2010 | |
| KR | 10-2010-0089632 A | | 8/2010 | |
| KR | 10-2010-0138128 A | | 12/2010 | |
| KR | 10-2012-0021899 A | | 3/2012 | |
| KR | 10-2012-0116215 A | | 10/2012 | |
| KR | 10-2014-0007546 A | | 1/2014 | |
| KR | 10-2016-0122657 A | | 10/2016 | |
| KR | 10-2016-0129386 A | | 11/2016 | |

OTHER PUBLICATIONS

Bernhardt Alginate hydroxyapatite scaffolds, J. Tissue Eng. Med, May (Year: 2008).*
Encapsulator B-395 May 2016.*
Wang Biointerphases, hydroxyapatite-alginate nanoparticles May 2015.*
Li, Hydroxyapatite biodegradable nanocomposite, p. 2828, Nov. 2003.*
Liu, Ceramic nanoparticles in polymer composites, Int'l J. Nanomedicine, p. 299 (Year: 2010).*
C.C. Ribeiro et al., 'Calcium phosphate-alginate microspheres as enzyme delivery matrices' *Biomaterials* vol. 25, No. 18, Dec. 2004, pp. 4363-4373.
Nemethova, V. et al., "Virbration Technology for Microencapsulation: The Restrictive Role of Viscosity" J. Bioproces. Biotech. (2015) vol. 5, Issue 1, an open access journal.
Encapsulator B-390/B-395 Pro Technical data sheet.
Encapsulator B-390/B-395 Pro.
International Search Report PCT/ISA/210 for International Application No. PCT/KR2018/004362 dated Jul. 12, 2018.
International Search Report PCT/ISA/210 for International Application No. PCT/KR2018/004363 dated Jul. 23, 2018.

* cited by examiner

*Primary Examiner* — Sarah Alawadi
*Assistant Examiner* — Thurman Wheeler
(74) *Attorney, Agent, or Firm* — Harness, Dickey & Pierce, P.L.C.

(57) ABSTRACT

A method for producing granules of a uniform size includes preparing an organic member solution, uniformly dispersing an inorganic member in the organic member solution at a weight ratio of 1 to 10 based on an organic member to form an organic-inorganic composite solution, spraying the organic-inorganic composite solution in an electrostatic charge manner, and polymerizing the sprayed organic-inorganic composite solution to form a hydrogel phase. The granules having a uniform size may be mass-produced in a short time and may be produced at a high yield. The method may be applied to a variety of fields, such as a pharmaceutical field, a medical field, a cosmetics field, and a food field and may replace a conventional spray drying method.

17 Claims, 57 Drawing Sheets

[FIG. 1A]
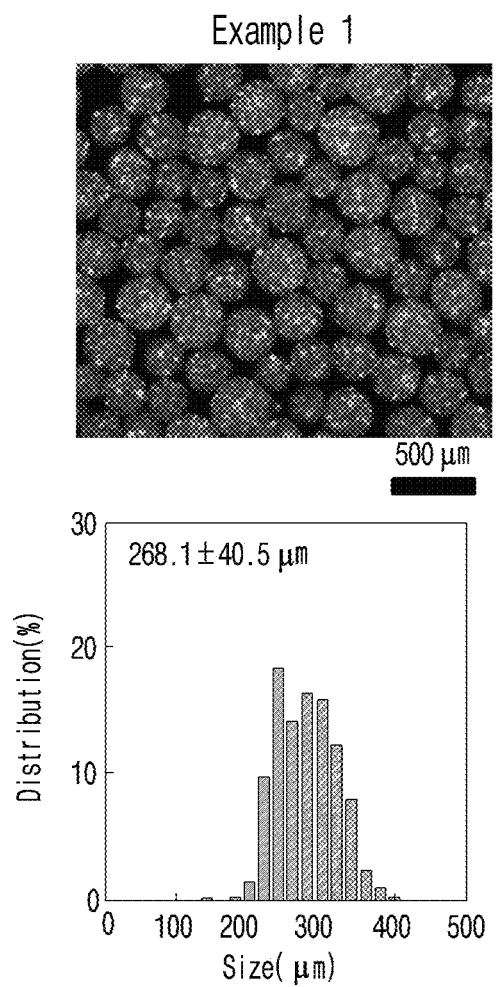

[FIG. 1B]
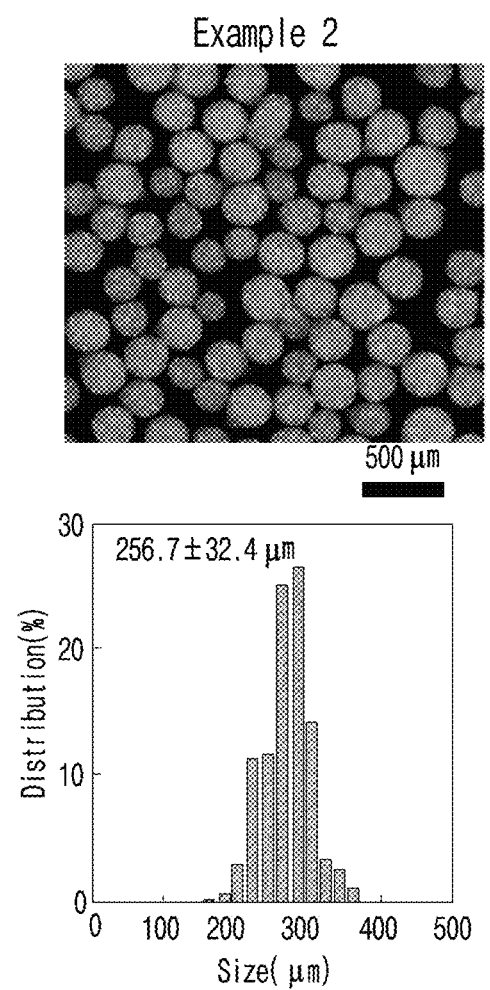

[FIG. 1C]
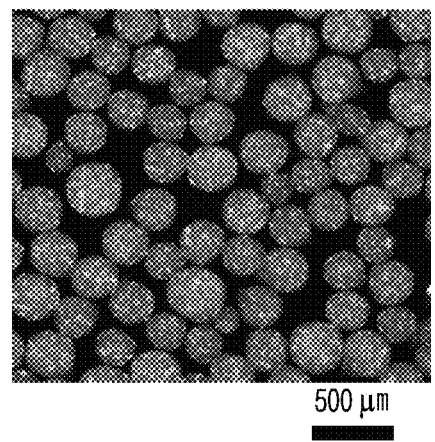
Example 3
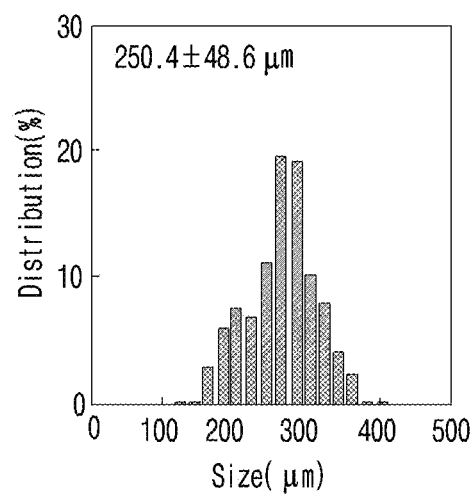
250.4±48.6 μm

[FIG. 1D]
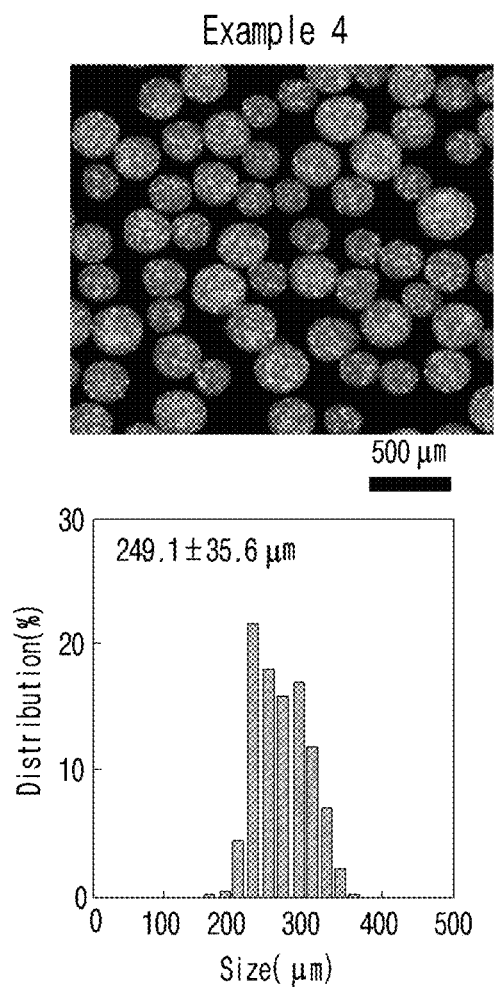

[FIG. 2A]
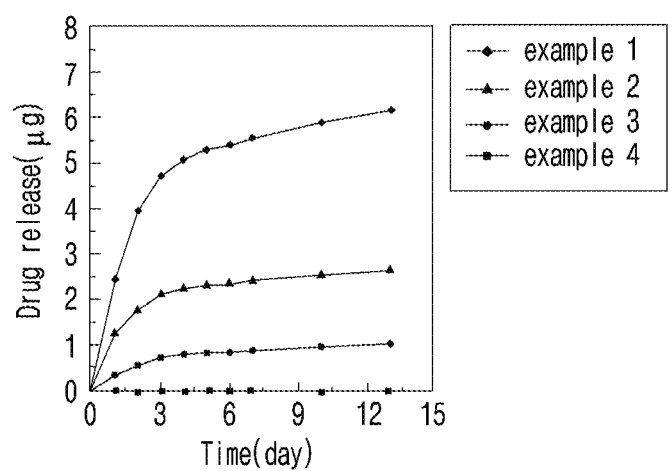

[FIG. 2B]
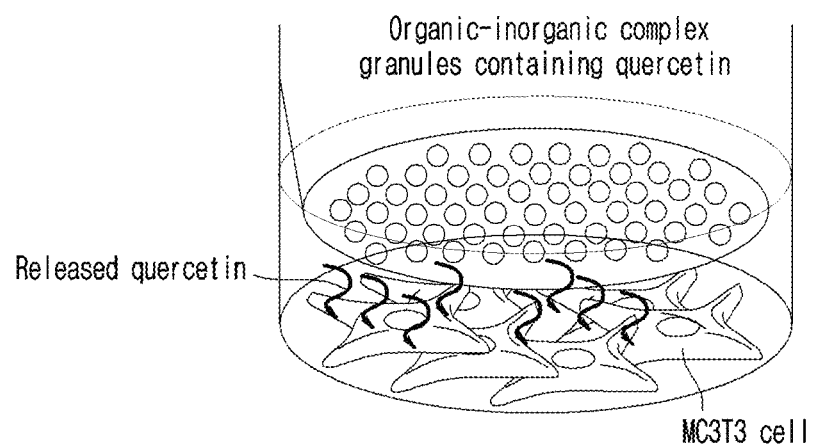

[FIG. 2C]
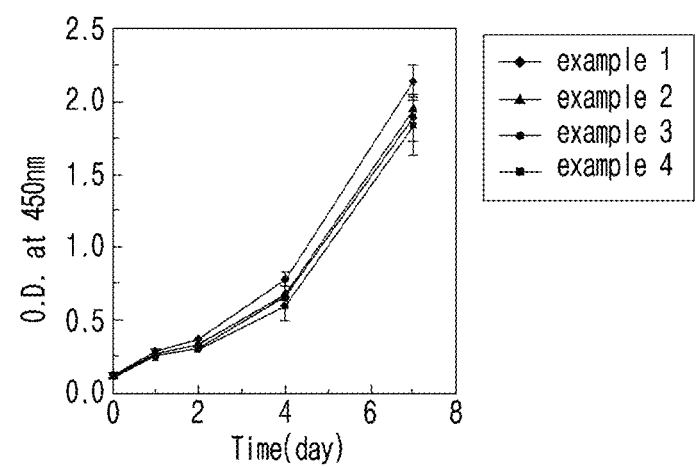

[FIG. 3A]
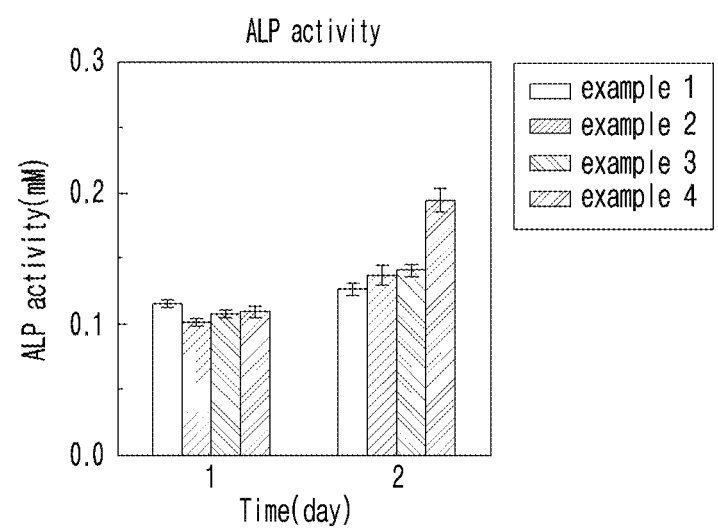

[FIG. 3B]
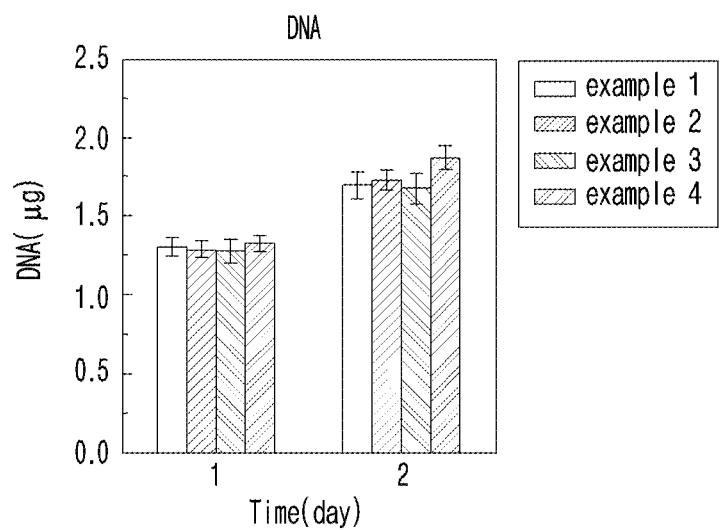

[FIG. 4]
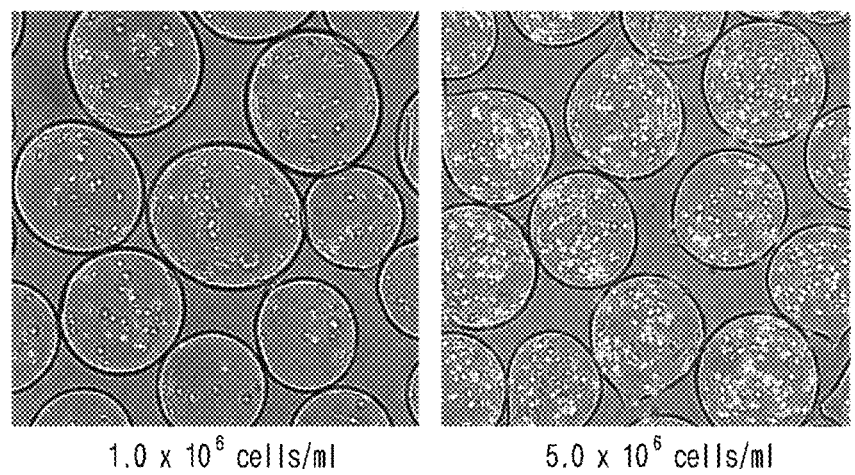

[FIG. 5A]
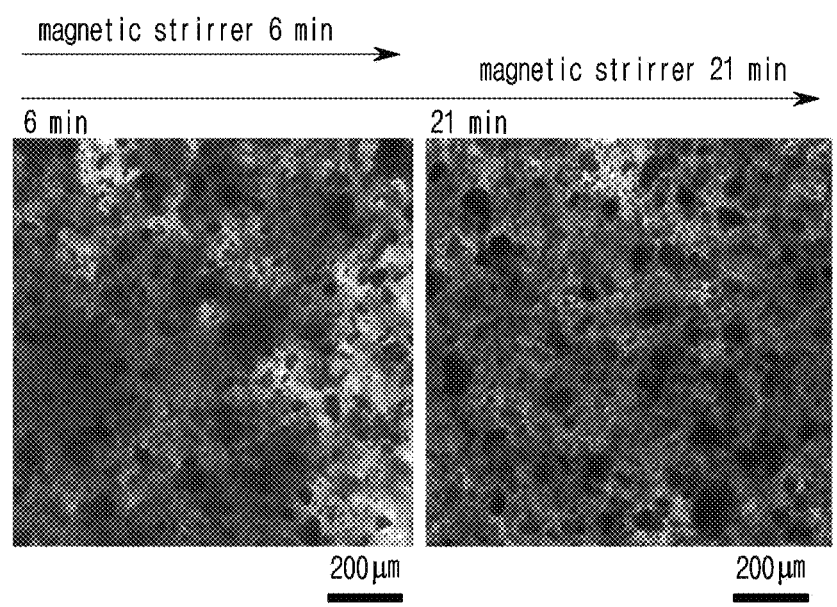

[FIG. 5B]
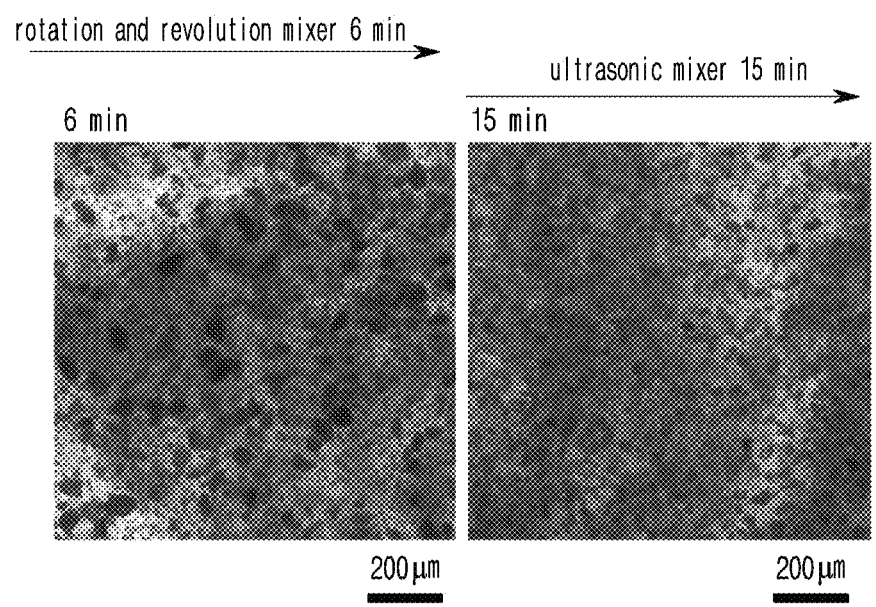

[FIG. 6A]
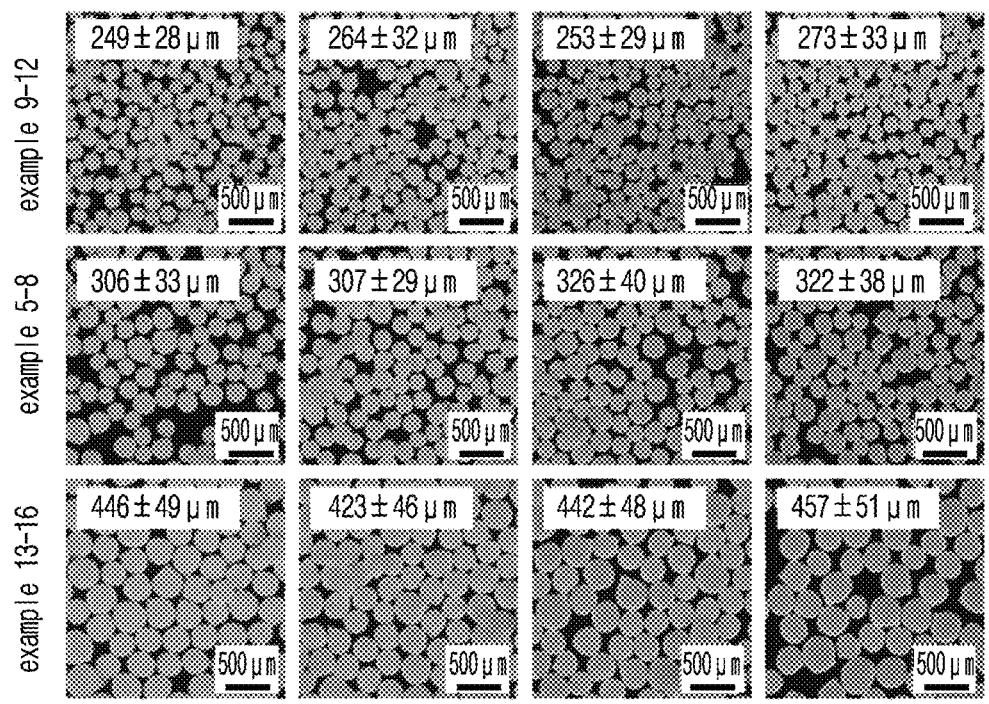

[FIG. 6B]
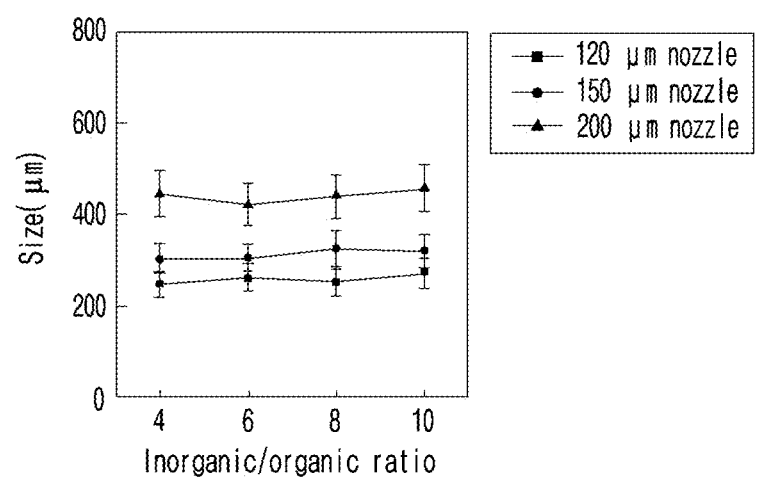

[FIG. 7]
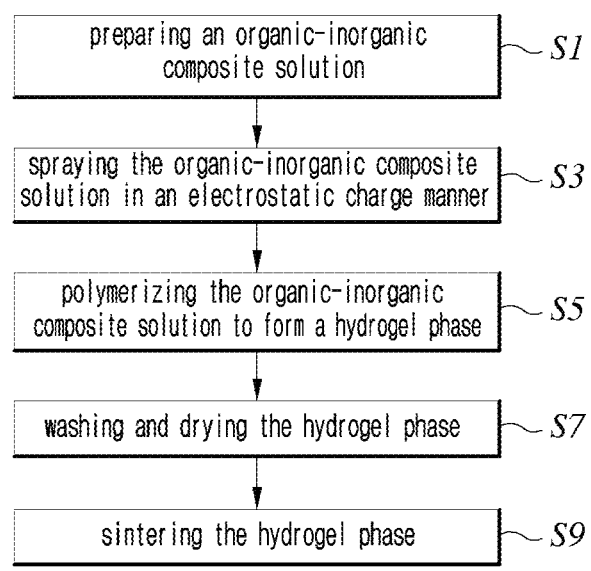

[FIG. 8]
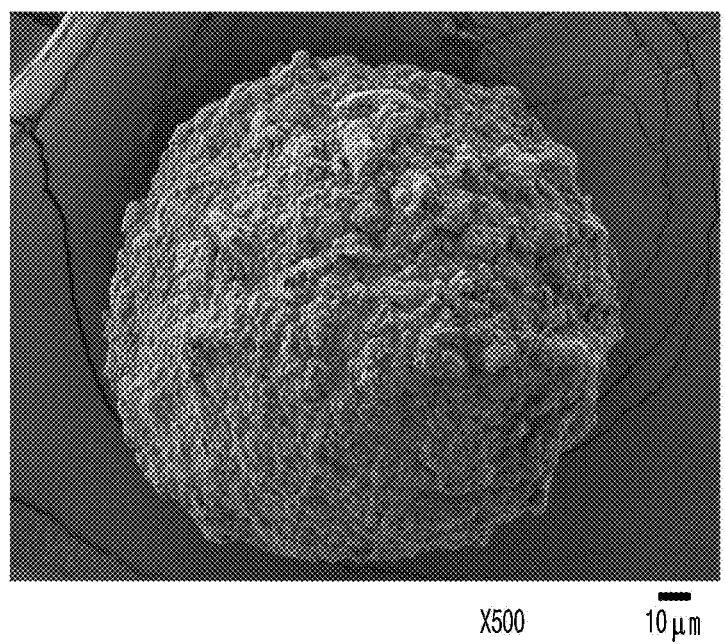

[FIG. 9]
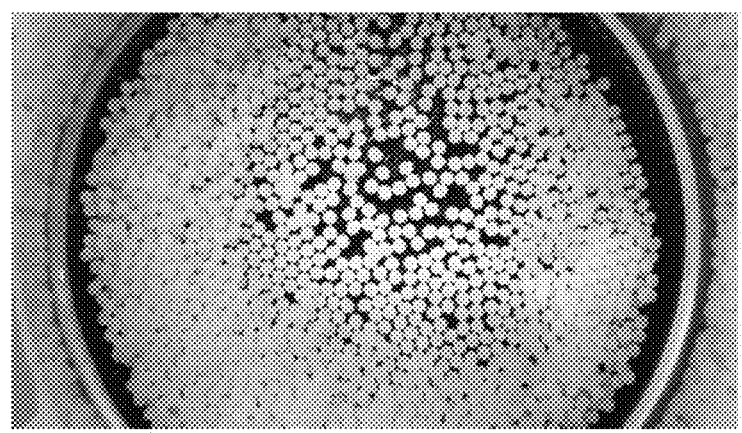

[FIG. 10]
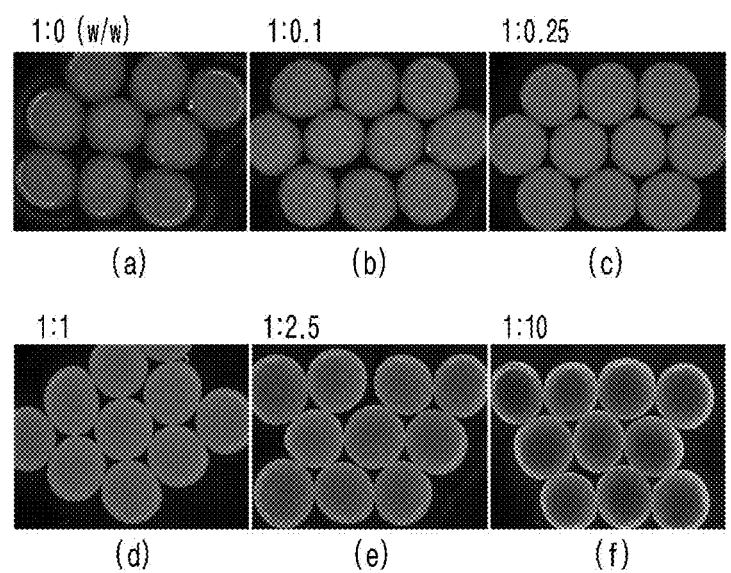

[FIG. 11]
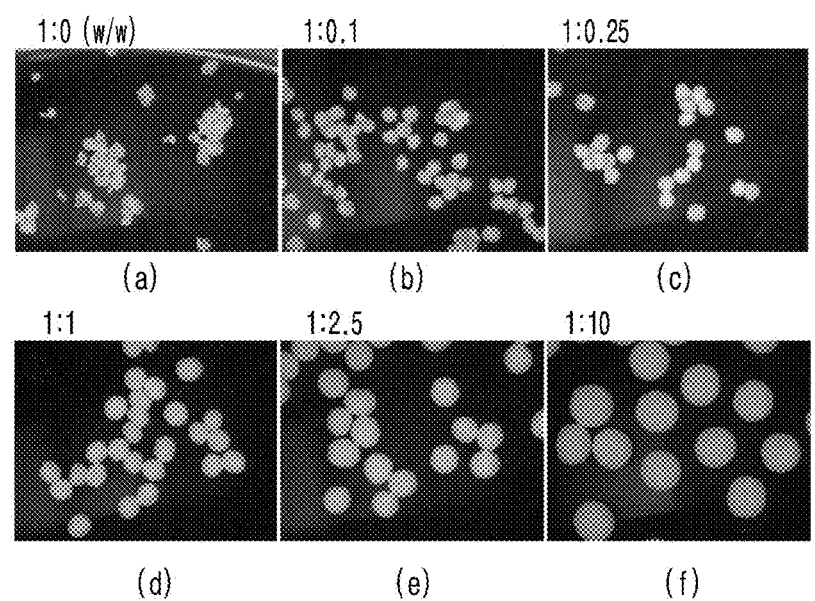

[FIG. 12]
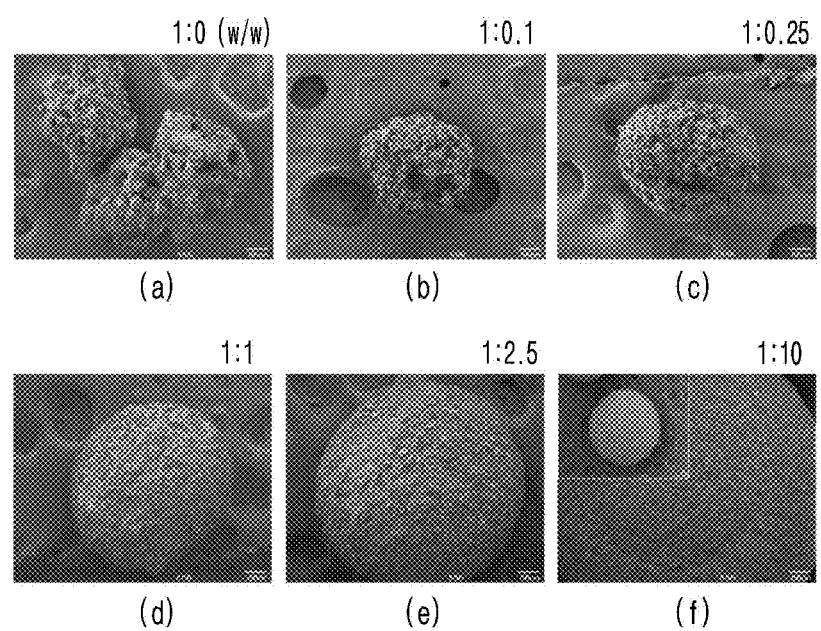

[FIG. 13]
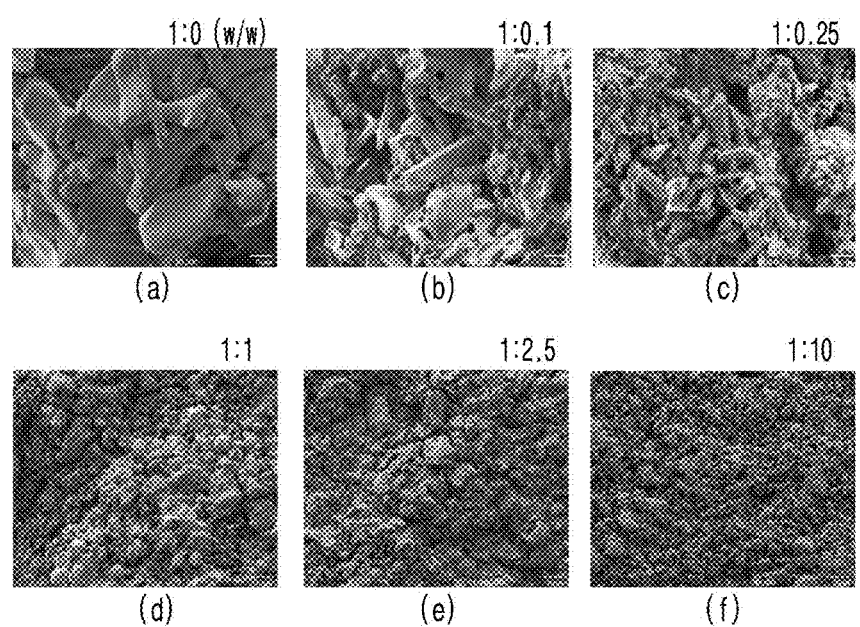

[FIG. 14A]
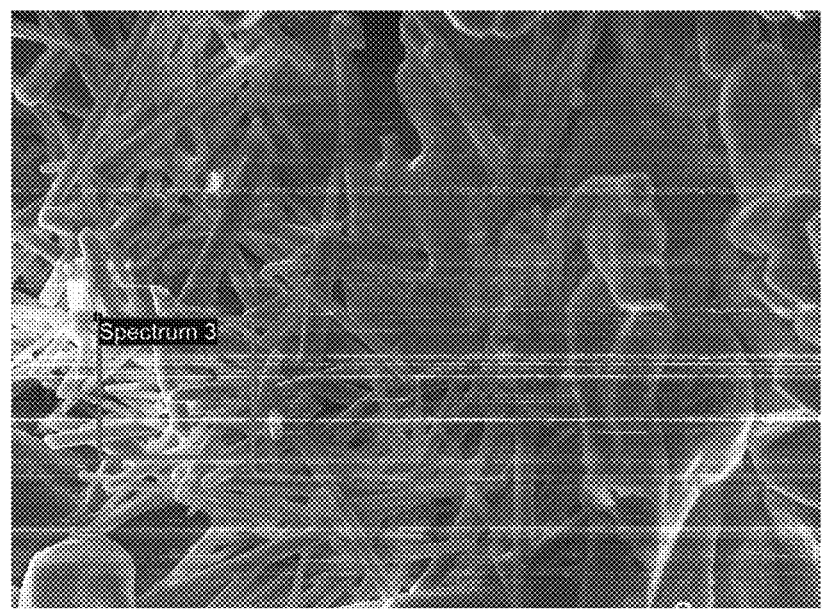
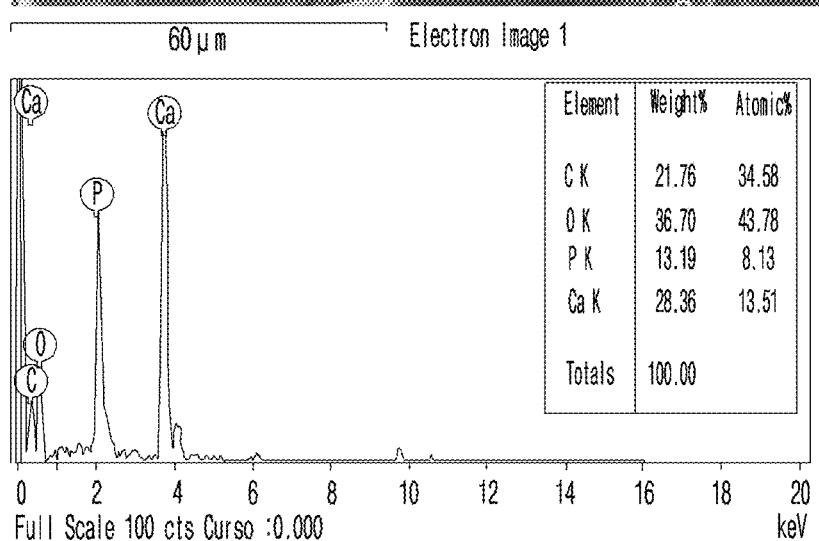

[FIG. 14B]
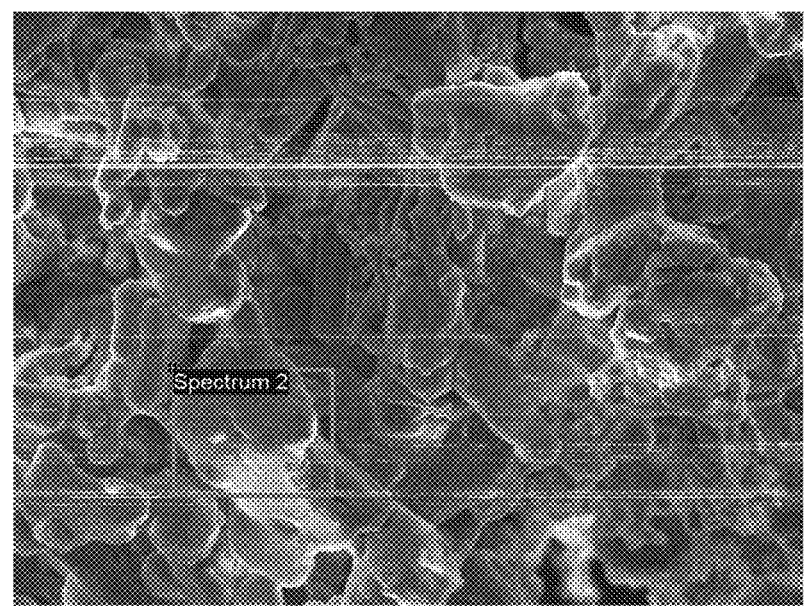
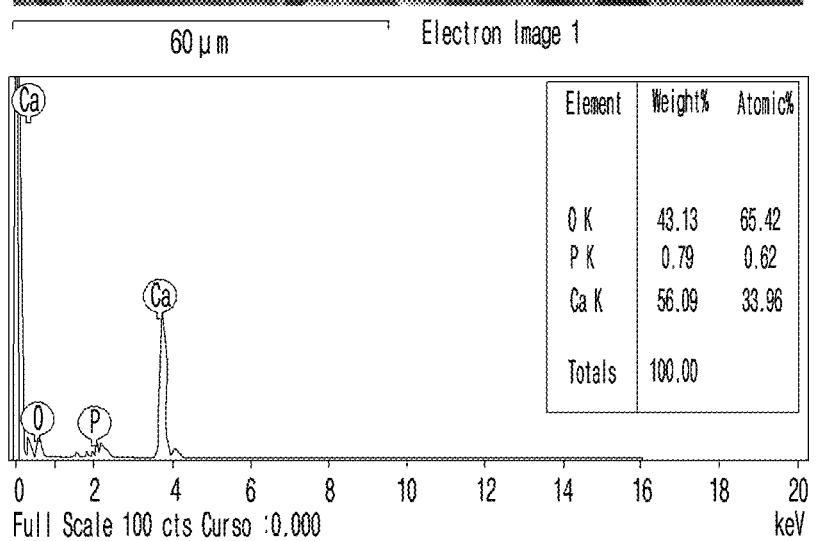

[FIG. 15]
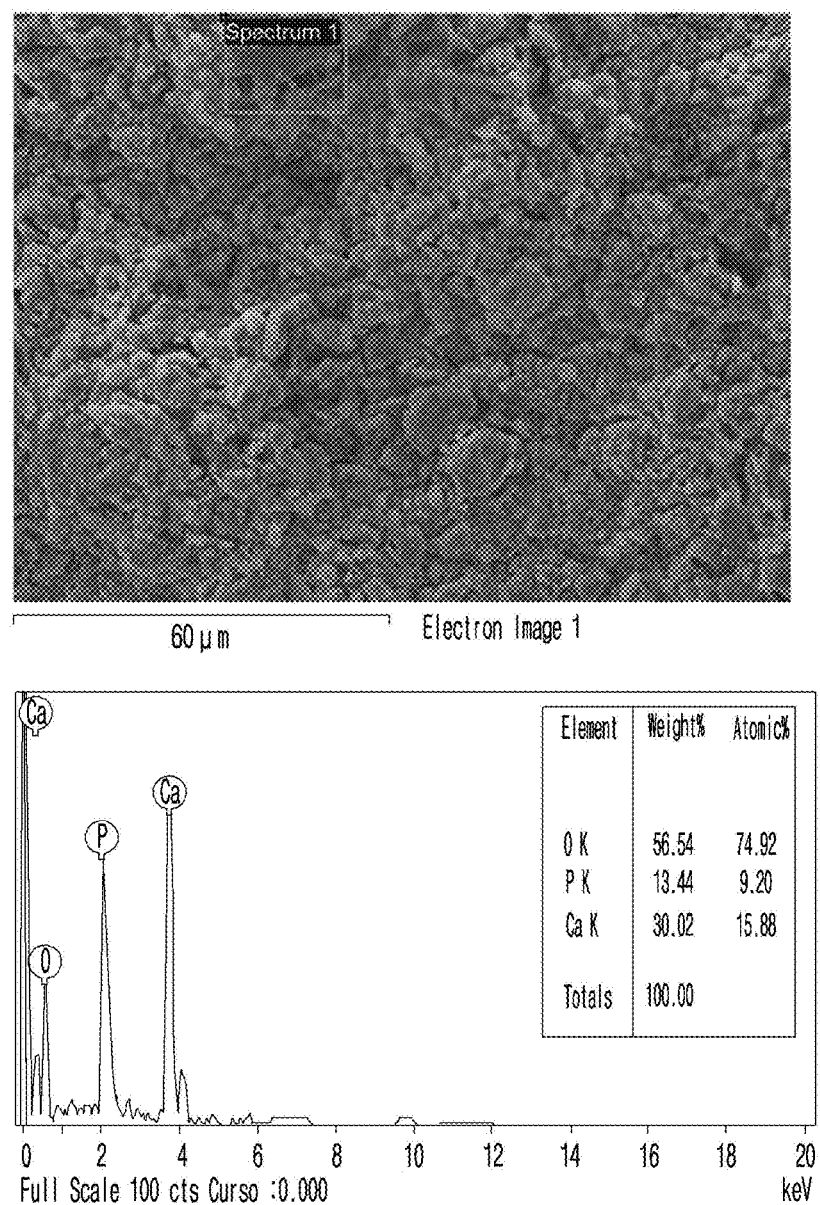

[FIG. 16]
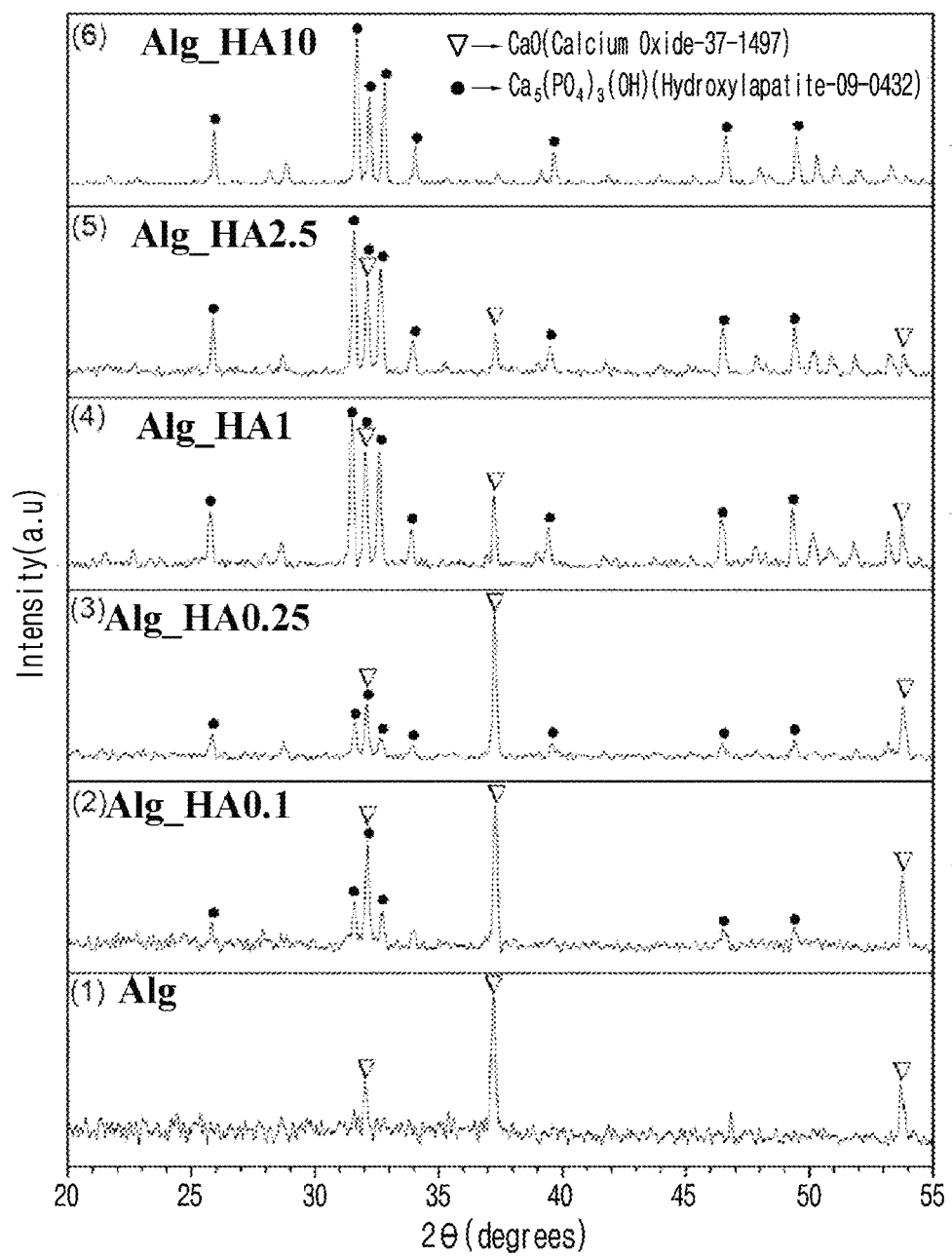

[FIG. 17]
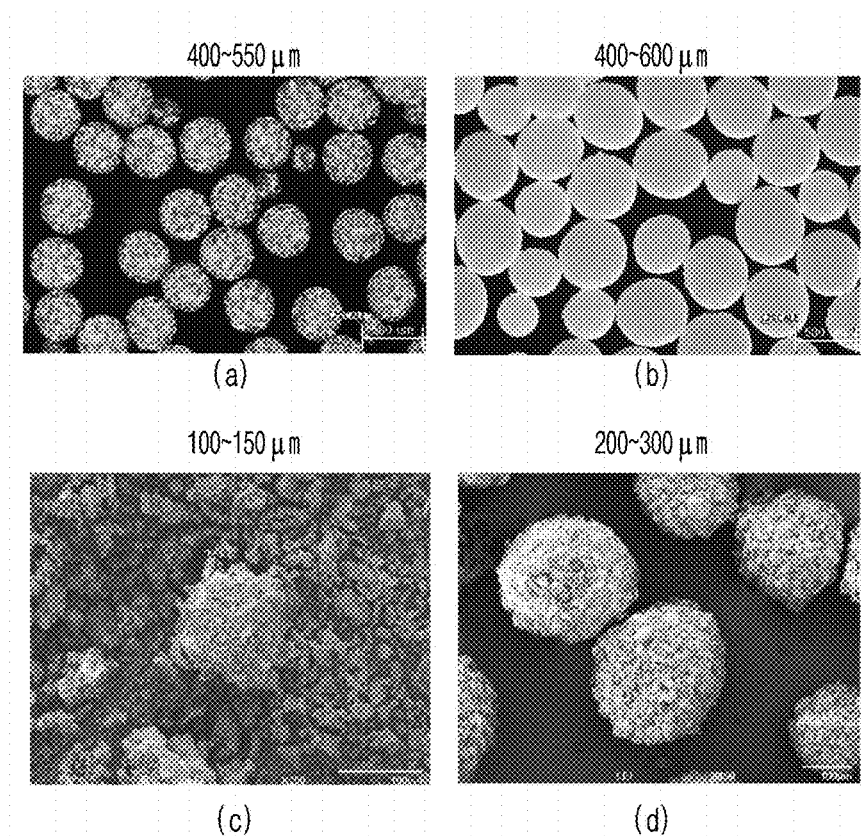

[FIG. 18]
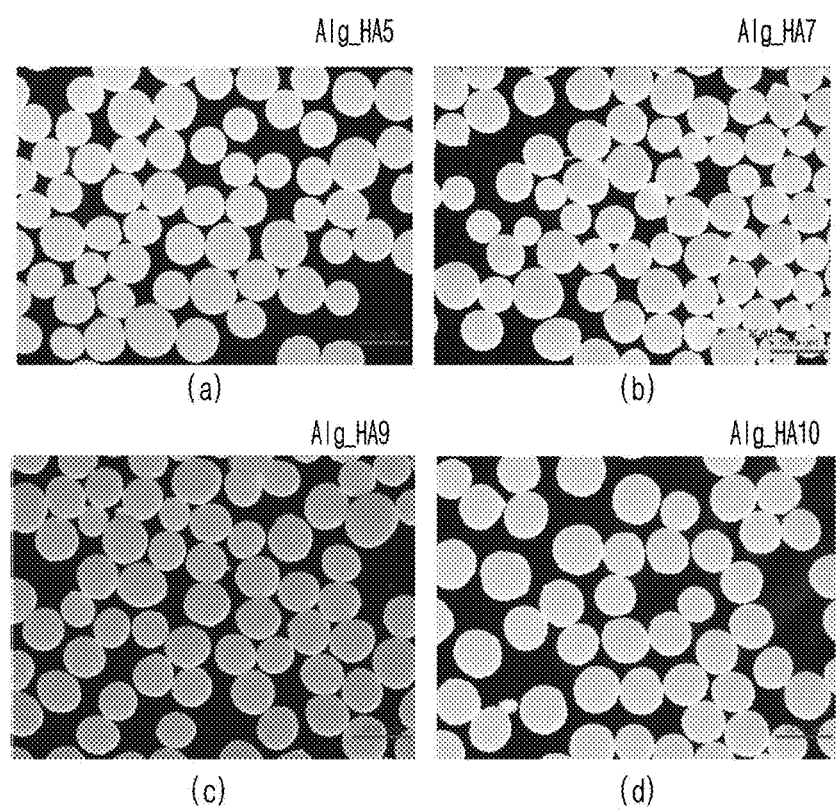

[FIG. 19]
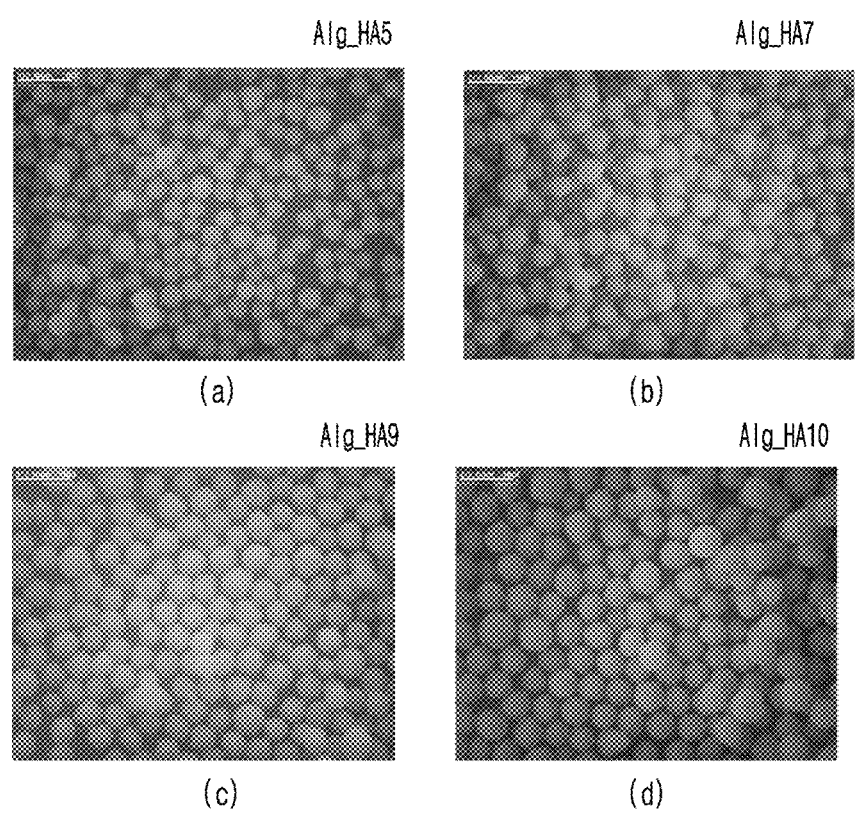

[FIG. 20]
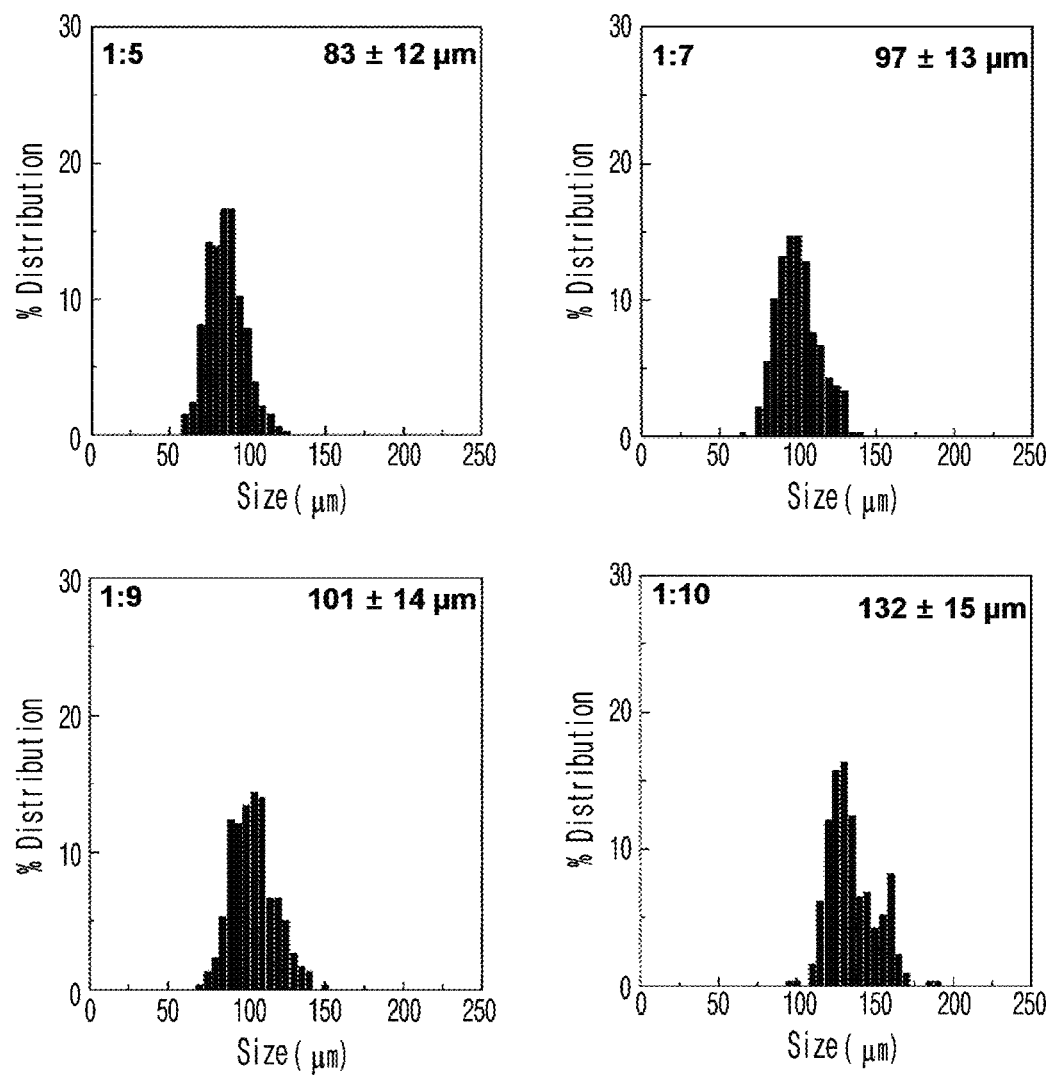

[FIG. 21]
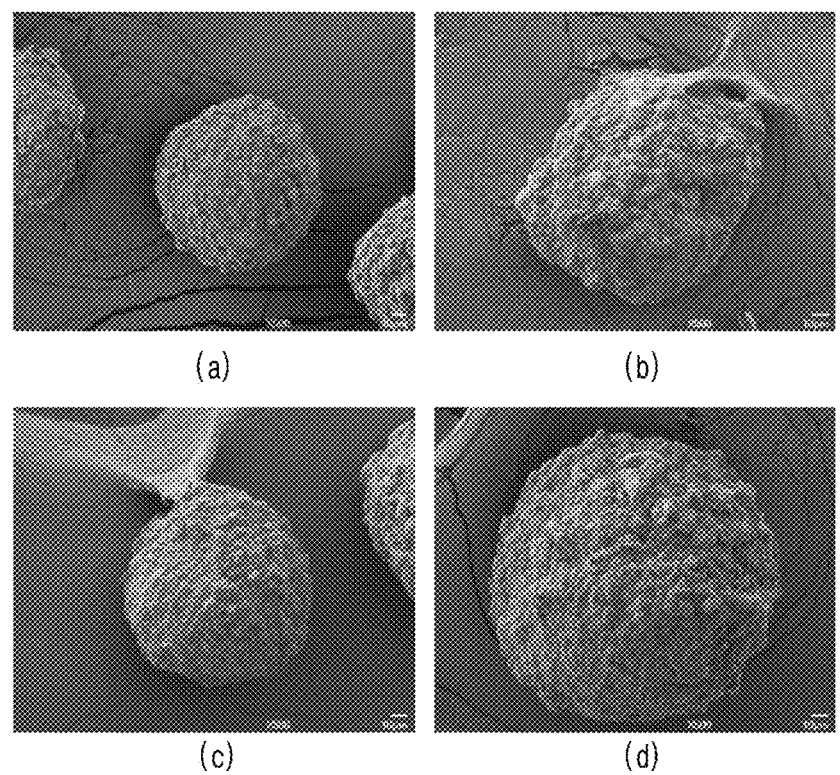

[FIG. 22]
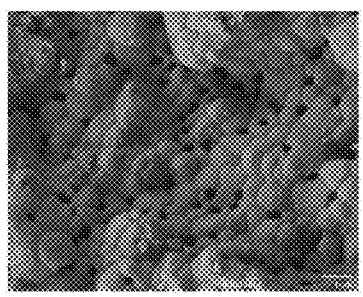 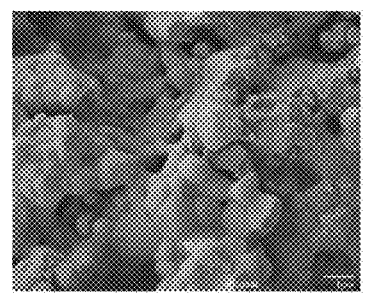
(a) (b)
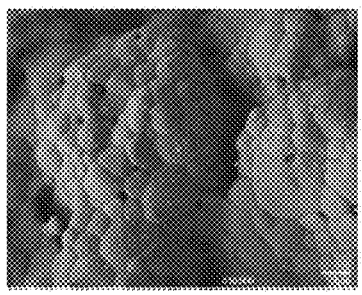 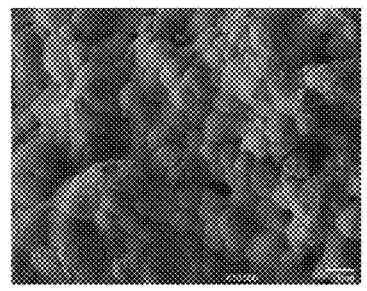
(c) (d)

[FIG. 23A]
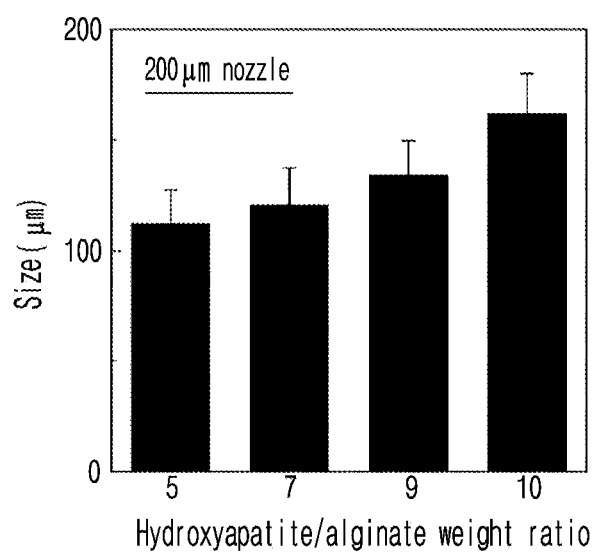

[FIG. 23B]
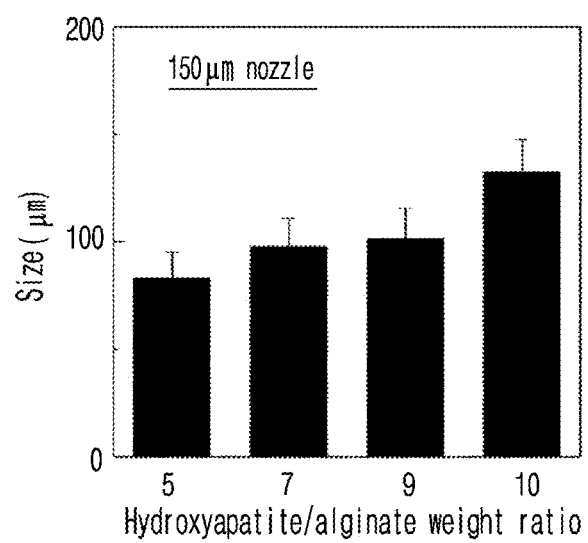

[FIG. 23C]
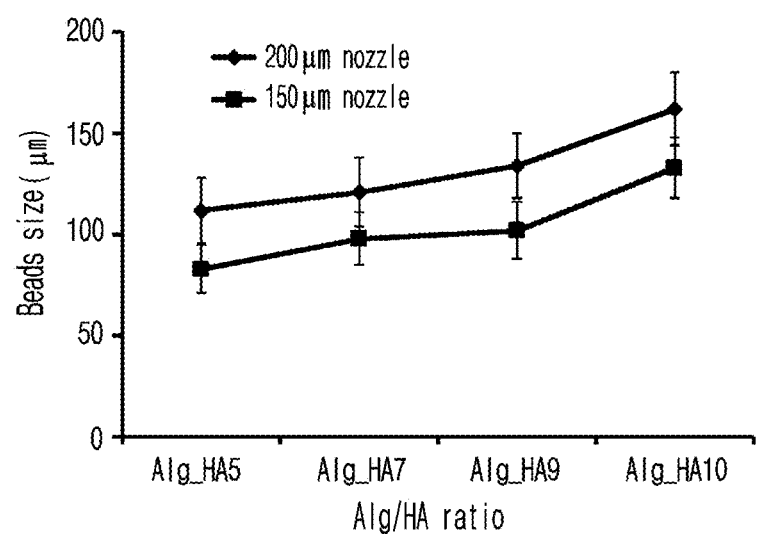

[FIG. 24A]
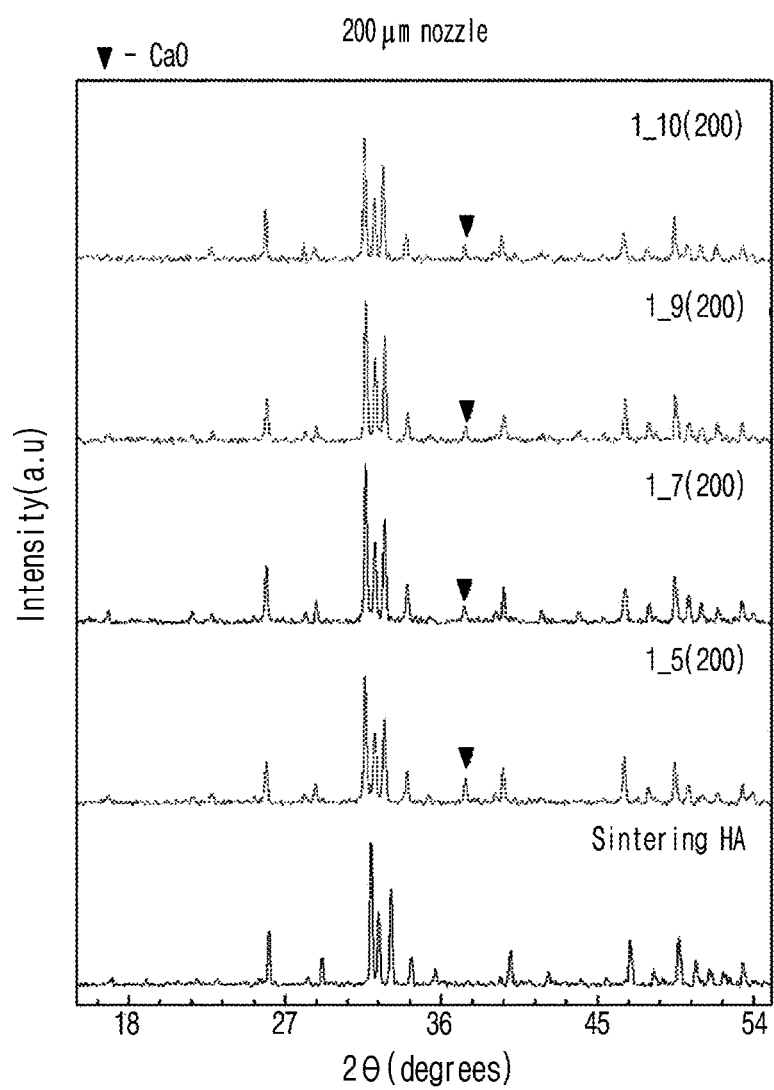

[FIG. 24B]
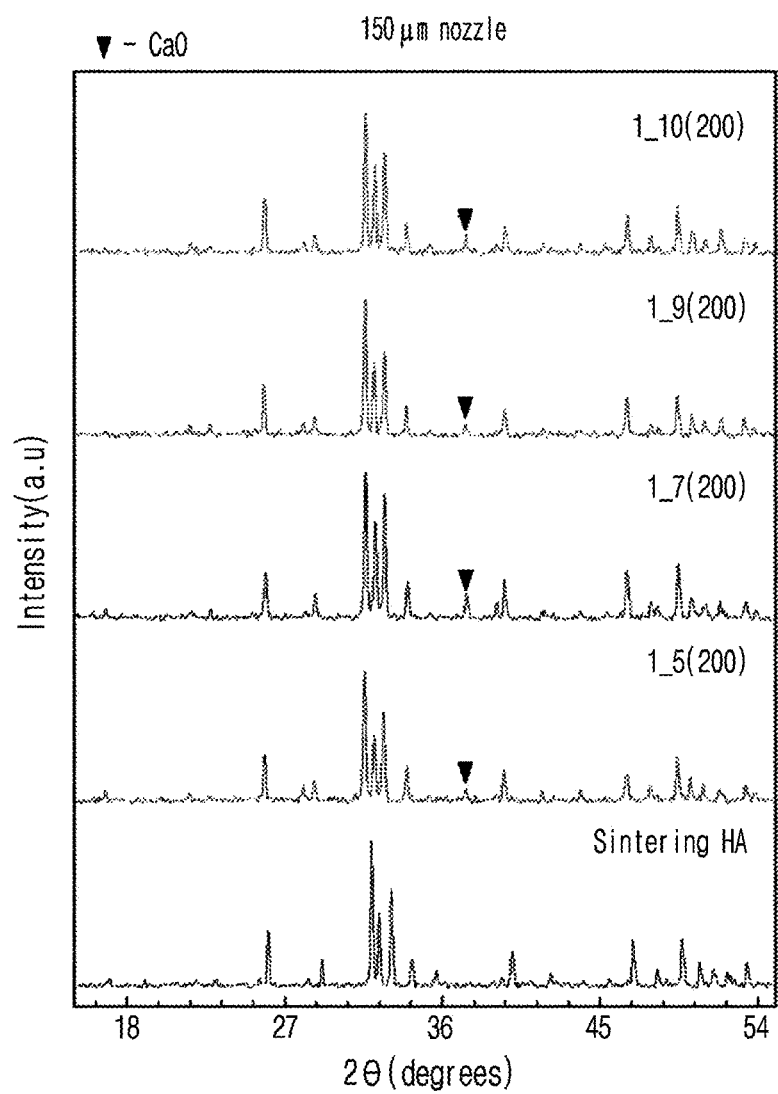

[FIG. 25A]
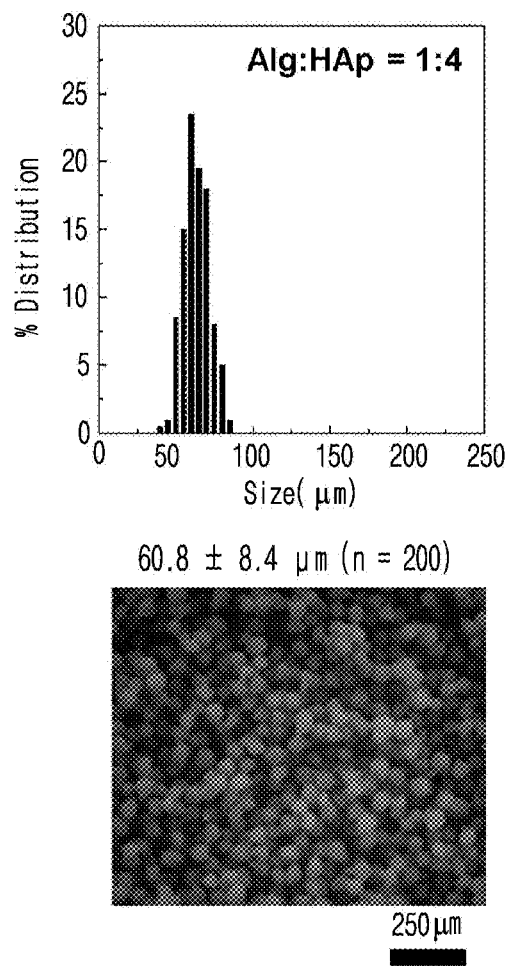

[FIG. 25B]
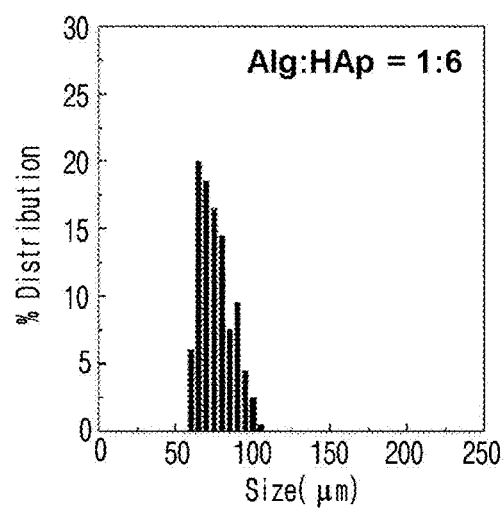
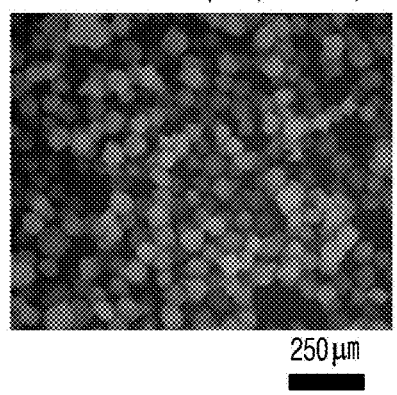

[FIG. 25C]
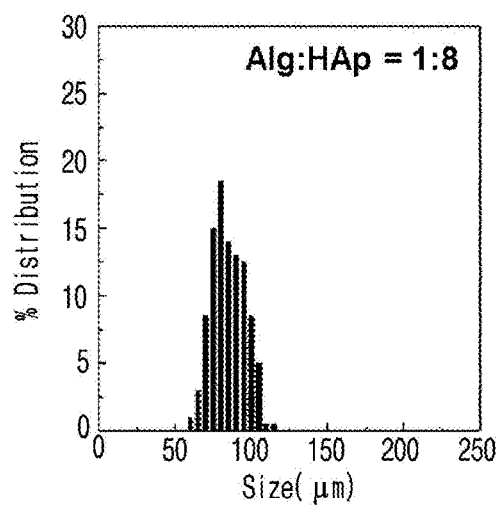
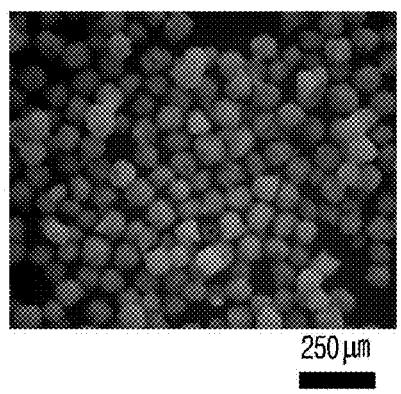

[FIG. 25D]
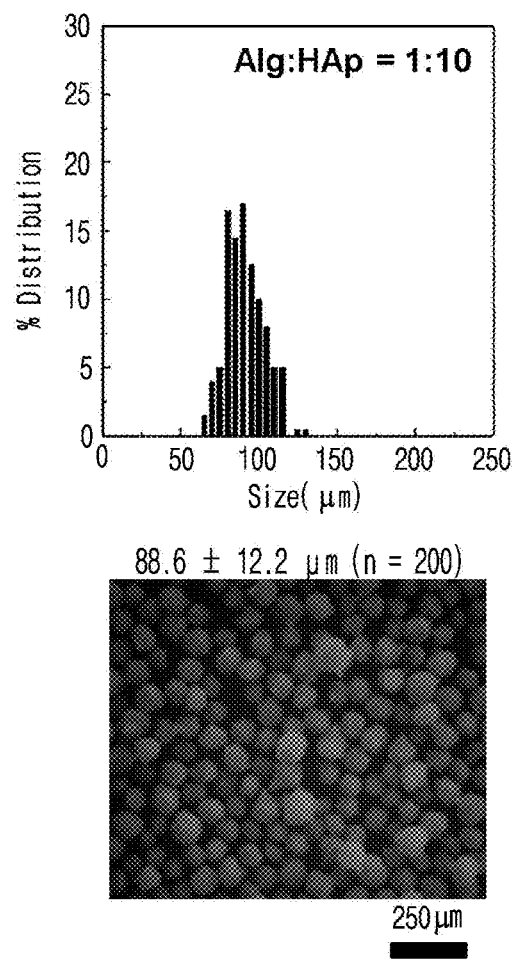

[FIG. 26A]
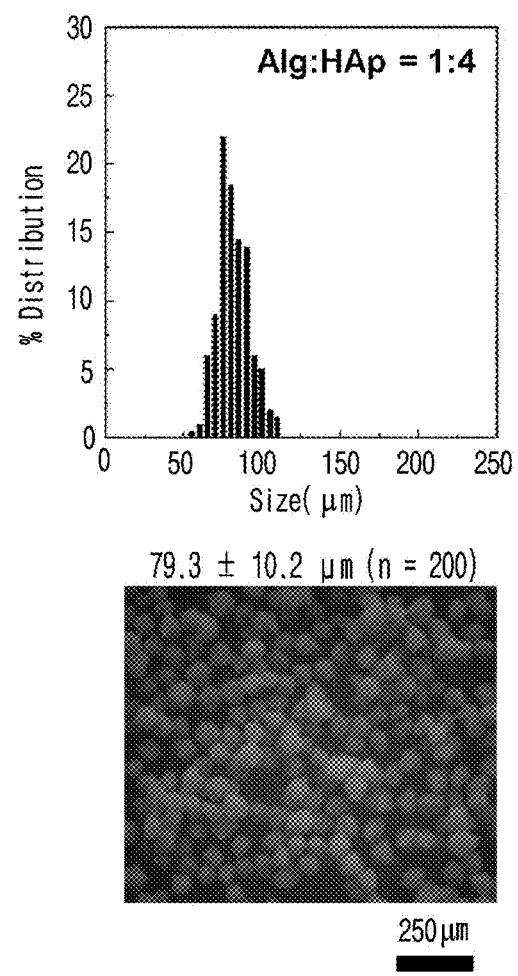

[FIG. 26B]
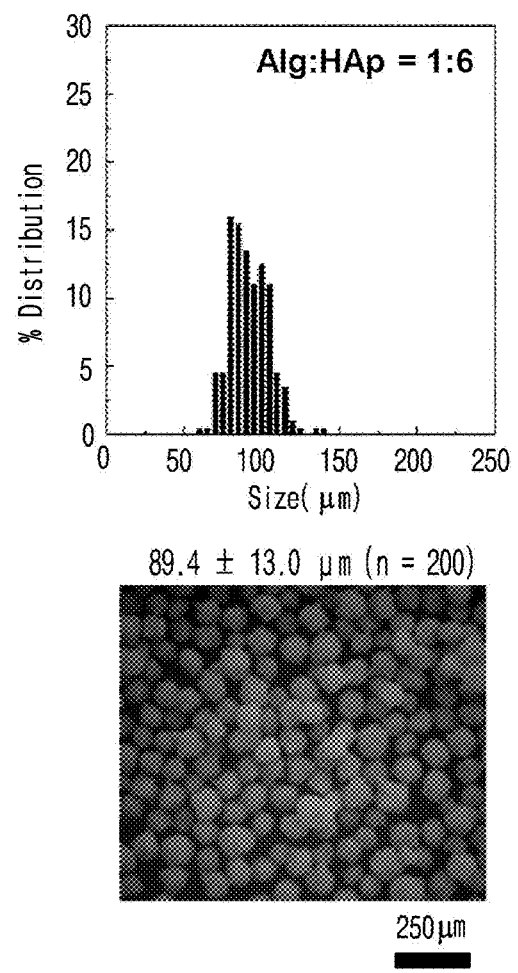

[FIG. 26C]
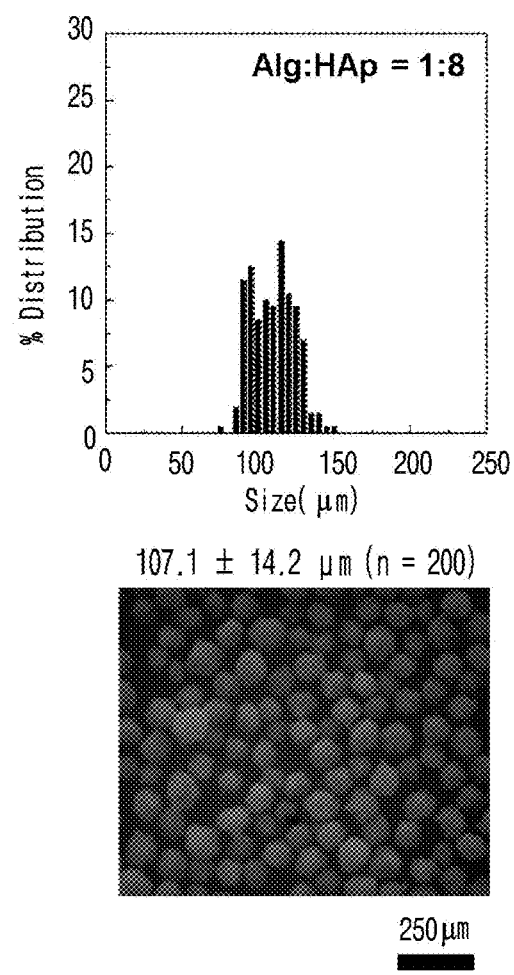

[FIG. 26D]
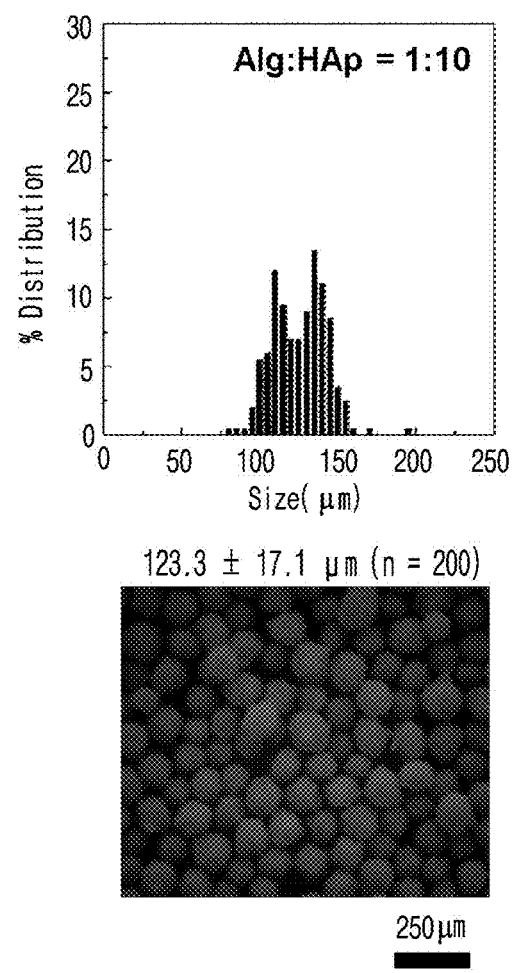

[FIG. 27A]
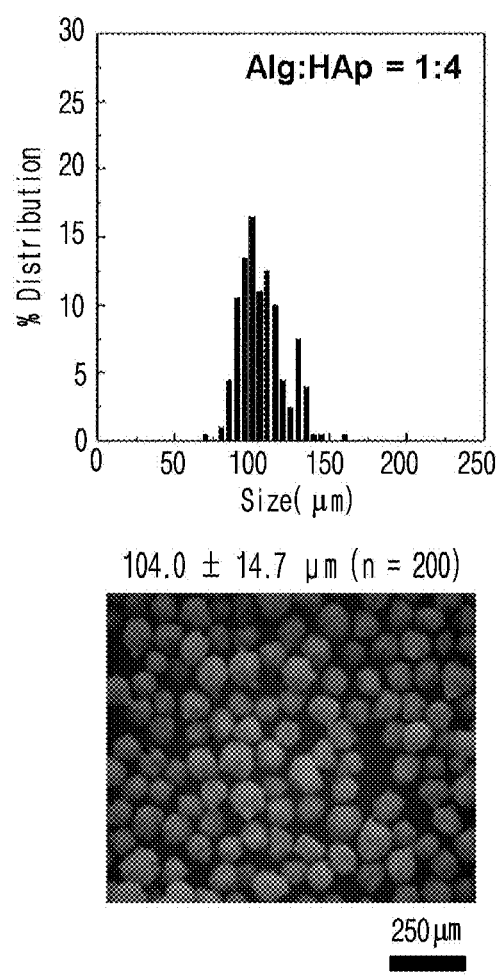

[FIG. 27B]
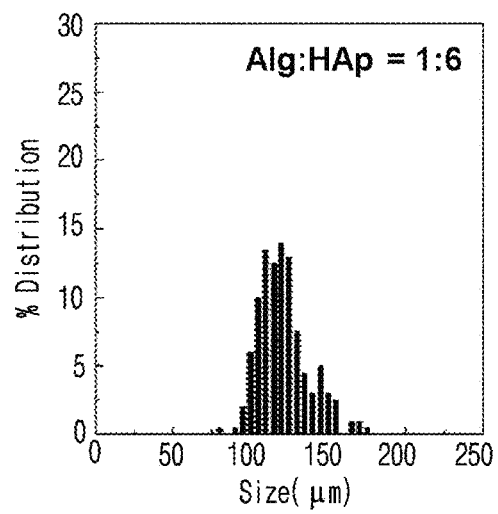
118.8 ± 16.3 μm (n = 200)
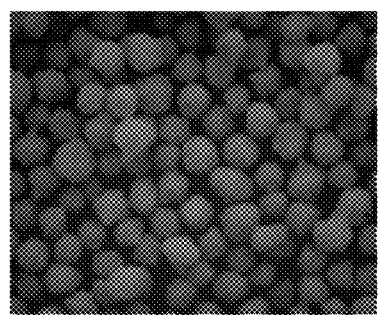
250 μm

[FIG. 27C]
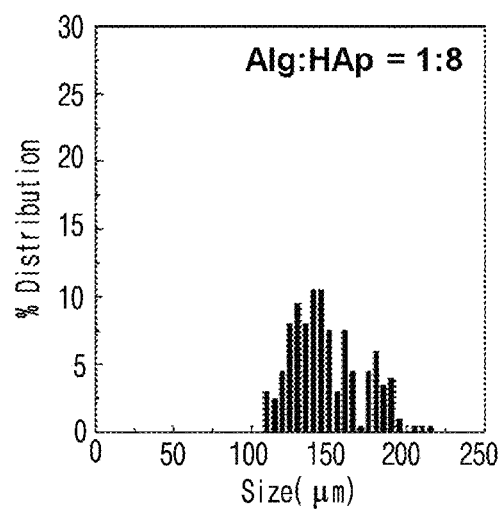
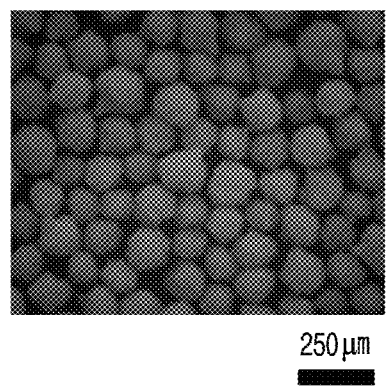

[FIG. 27D]
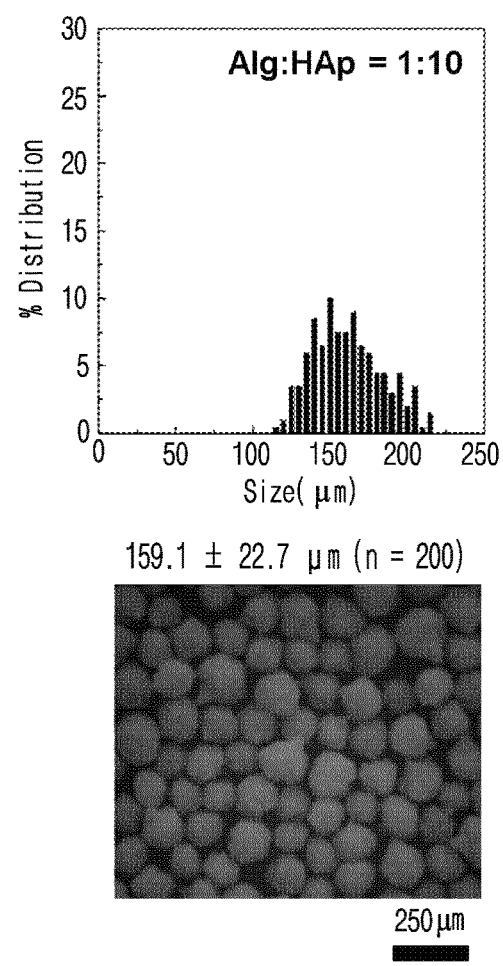

[FIG. 28A]
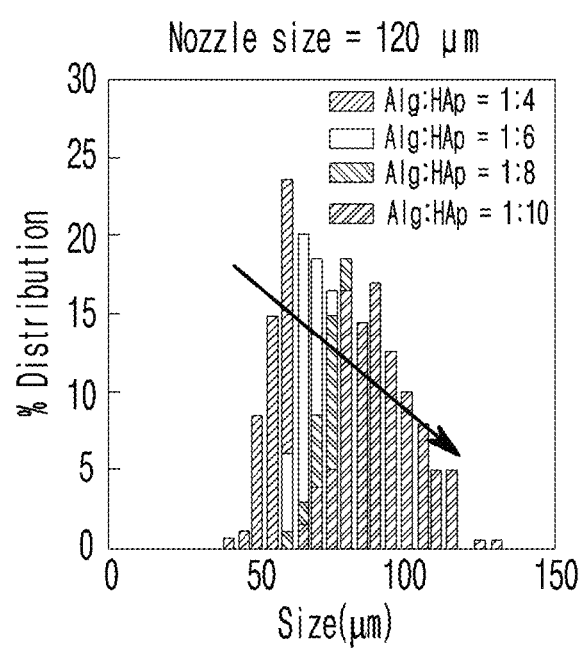

[FIG. 28B]
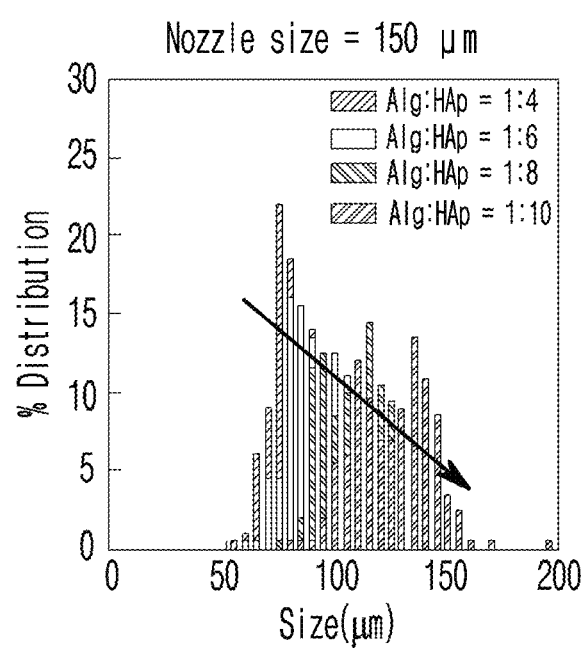

[FIG. 28C]
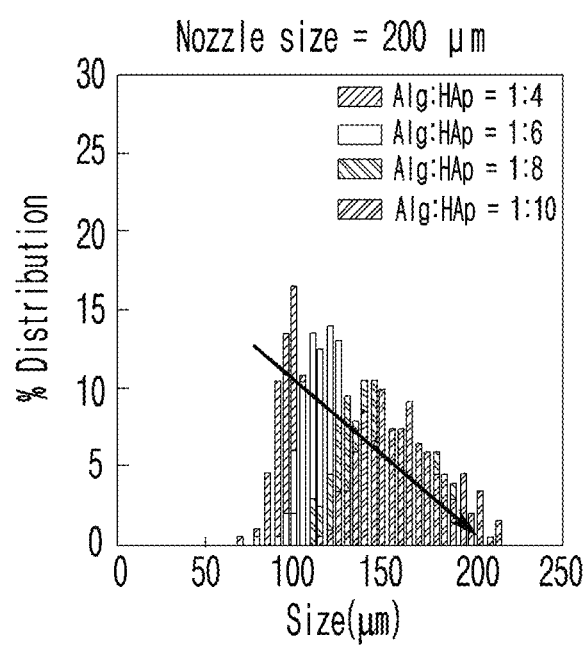

[FIG. 29A]
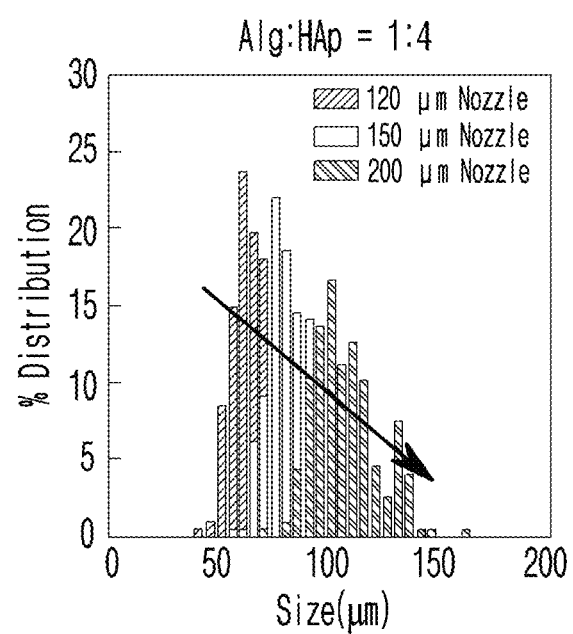

[FIG. 29B]
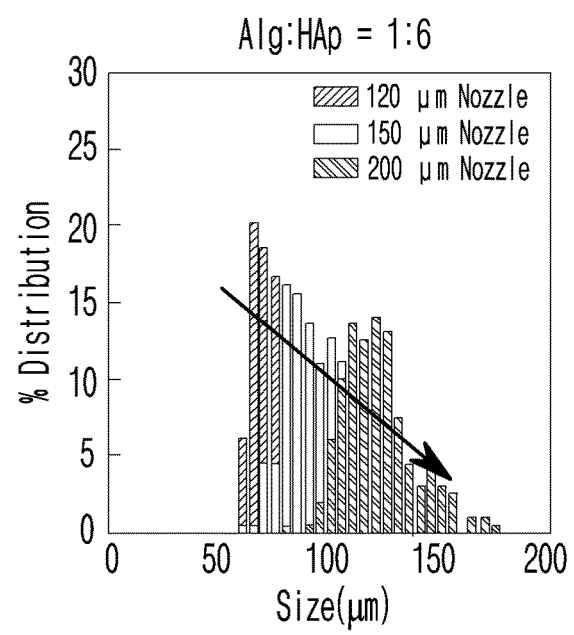

[FIG. 29C]
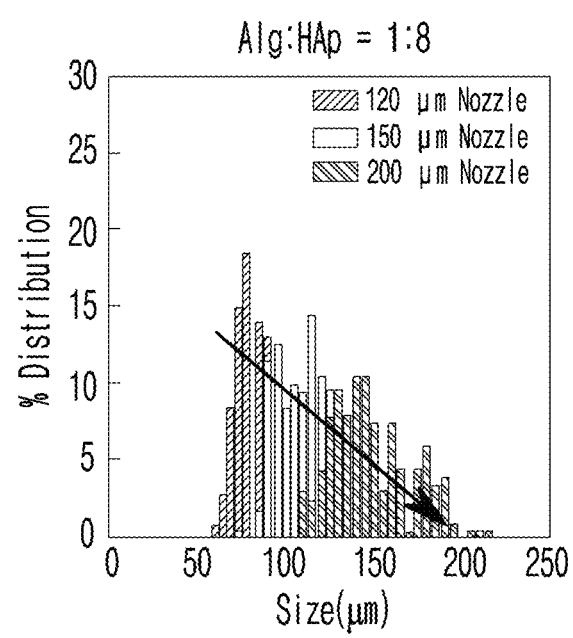

[FIG. 29D]
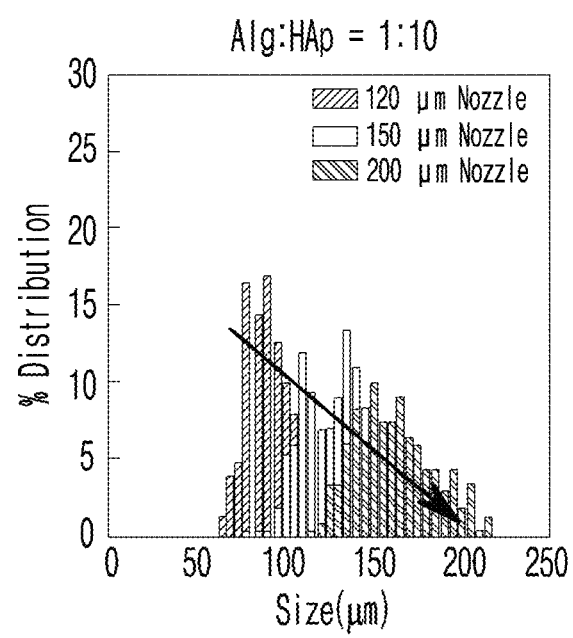

[FIG. 30A]
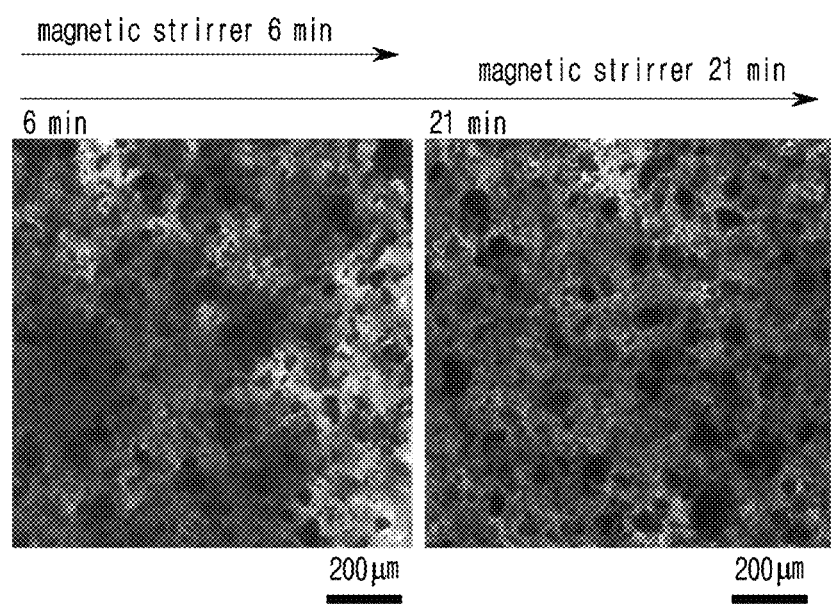

[FIG. 30B]
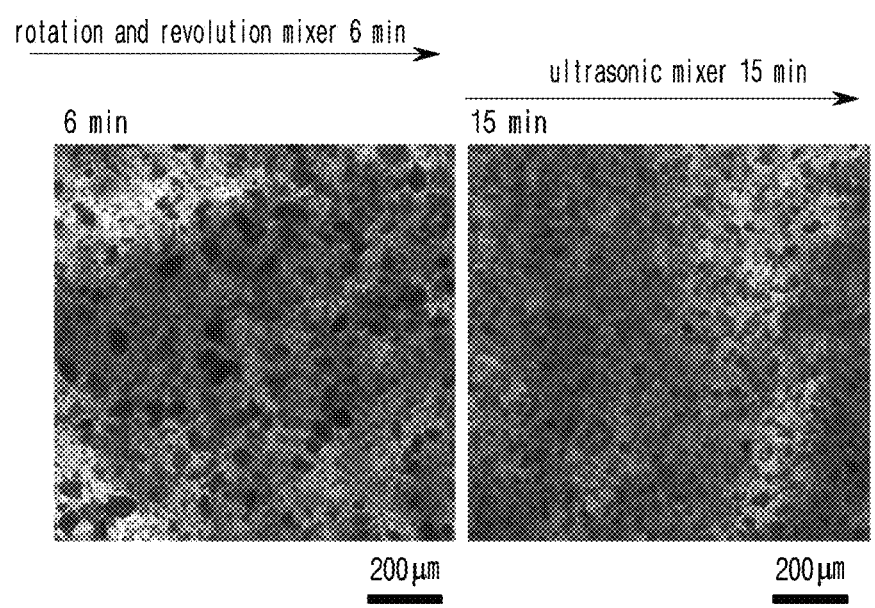

MANUFACTURING METHOD FOR GRANULE

RELATED APPLICATION

This application is a continuation-in-part of PCT International Application No. PCT/KR2018/004362 which has an International filing date of Apr. 13, 2018, and which claims priority to Korean Patent Application No. 10-2017-0048463, filed on Apr. 14, 2017, and Korean Patent Application No. 10-2017-0099806, filed on Aug. 7, 2017, and PCT International Application No. PCT/KR2018/004363 which has an International filing date of Apr. 13, 2018, and which claims priority to Korean Patent Application No. 10-20170048463, filed on Apr. 14, 2017, the entire contents of each of which are incorporated herein by reference.

TECHNICAL FIELD

The present invention relates to a method for producing granules.

BACKGROUND ART

Bio-ceramic represented by a calcium phosphate system is used as a bone graft material or a bone filler in various forms such as powder, granules, paste, and support as a bioceramic alone or a ceramic-organic polymer organic-inorganic composite. Particularly, granules are easily applied either alone or in the form of a paste to irregular defect regions, and thus, are widely used in the fields of dentistry, orthopedics, and the like. In addition, in order to increase the biofunctionality of the granules, a variety of drugs are adsorbed onto ceramic or organic-inorganic composite granules and used.

In order to produce such ceramic or organic-inorganic composite granules, a spray drying method and a chemical reaction method (emulsion, sol-gel method, and the like) are generally used. The spray drying method has an advantage in that a large amount of granules may be produced in a short time, but since the size distribution of the granules is large, there is a disadvantage in that the production yield for a required size is very low. Meanwhile, the chemical reaction method has an advantage in that granules having a relatively uniform size may be produced. However, there is a disadvantage in that mass production is difficult and the production process thereof is complicated.

Regarding a bone filler supported with a sustained release osteoporosis treatment agent, Korean Patent Laid-Open No. 10-2010-0026910 discloses a bone filler used for fracture patients caused by osteoporosis by adding calcium phosphate microspheres supported with alendronate, an osteoporosis treatment agent, to a human demineralized bone matrix. However, there are disadvantages in that it is difficult to mass-produce microspheres in a short time obtained by a sol-gel process, and that it is not easy to control the size of the produced microspheres.

Also, Korean Patent Laid-Open No. 10-2012-0021899 discloses a method for producing a porous organic-inorganic hybrid, and more specifically, a method for producing a porous organic-inorganic hybrid material, the method including supporting an ionic compound or a polar compound on the porous organic-inorganic hybrid. However, with the above technique, it is not possible to obtain granules having a uniform particle size, and there is a problem in mass producing the granules.

Electrospraying in an electrostatic charge manner is a method of atomizing a liquid by an electric force (electric field). Liquid droplets formed by electrospraying have attracted attention as a useful nanotechnology in recent years because they have a high chargeability and have the advantage of preventing aggregation by their own dispersion. Particularly, the electrospraying technology is expected to be applied in various fields because it is possible to deposit fine and complex structures with inexpensive equipment and a simple operation in the atmosphere.

An example of an electric spraying apparatus using an electrostatic method as described above may be a micro-granule coater. The micro-granule coater is usually applied to an organic matter. That is, forming granules using a polymer and a hydrogel and forming core-shell granules containing oil or various drugs therein are applied in the field of pharmaceutical, chemical, cosmetics, food, agricultural, and the like for the purpose of delivering an active ingredient. Particularly, a micro-granule coater capable of encapsulation is provided to implement effects such as aging enhancement, storage stability, and blocking of harmful substances, thereby being applied to the food product industry. In addition, effects such as release control, solubility and osmotic enhancement, and the like have been implemented to be applied to the pharmaceutical industry. In addition, various effects are implemented in vivo testing and applied to the bio-medicine industry. However, when producing granules using a micro-granule coater, the viscosity of a raw material may be high, or in the case of a material prone to aggregation, problems such as nozzle clogging may occur.

Accordingly, the present inventors have conducted studies on a method for producing granules capable of producing granules having a uniform size in a short time and completed the present invention. A specific application example thereof may include a method for producing granules applicable to organic-inorganic composite granules, which are highly applicable as a bone graft material and a bone filler by increasing the content of an inorganic members (for example, a ceramic member).

PRIOR ART DOCUMENT

Korean Patent Laid-open Publication No. 10-2010-0026910
Korean Patent Laid-open Publication No. 10-2012-0021899

DISCLOSURE

Technical Problem

An object of the present invention is to provide a method for producing granules, and more specifically, to a method for producing spherical ceramic granules, the method which may be applied to a method for producing organic-inorganic composite granules having a uniform size and including an inorganic matter and to medicinal and cosmetics materials, capable of controlling the size of the granules, and mass-producing granules having a uniform size in a short time.

Technical Solution

To this end, the present invention provides a method for producing granules, the method characterized by including preparing an organic member solution, uniformly dispersing an inorganic member in the organic member solution at a weight ratio of 1 to 10 based on an organic member to form an organic-inorganic composite solution, spraying the organic-inorganic composite solution in an electrostatic charge manner, and polymerizing the sprayed organic-inorganic composite solution to form a hydrogel phase.

In addition, the present invention provides a method for producing granules, the method characterized by further including washing and drying the formed hydrogel phase formed as described above and sintering the washed and dried hydrogel phase.

Advantageous Effect

The method for producing granules of the present invention has an effect in that the size of granules produced is uniform and also, when a functional member is supported, sustained release properties are obtained. In addition, there is an advantage in that cell culture is easy. Furthermore, the production method of the present invention has advantages in organic-inorganic composite granules having a uniform size are mass-produced in a short time, and the granules are produced at a high yield. Accordingly, organic-inorganic composite granules and the production method thereof according to the present invention have an advantage of being applicable to various fields such as a pharmaceutical field, a medical field, a cosmetics field, and a food field.

In addition, the method for producing granules of the present invention has an advantage in that granules are produced by efficiently using a prepared raw material, thereby producing spherical ceramic granules at a high yield, and an advantage in that a micro-granule coater of an electrostatic charge manner is used, thereby producing a large amount of spherical granules having a uniform size in a short time.

Also, the production method of the present invention has an advantage of, with the control of the process setting of a micro-granule coater excluded, being able to control the composition ratio including calcium oxide, porosity between particles, pore structure, crystal phase and granule size according to change in the content of components contained in an organic-inorganic composite solution prepared through a sintering process performed in forming ceramic beads.

Furthermore, unlike a typical spray drying method, the production method of the present invention may include an oxide such as calcium oxide (CaO) generated by polymerizing and sintering an organic-inorganic composite solution. Accordingly, there is an advantage of being easily used in the medical field, such as a bone filler, a bone graft material, and filler.

Also, the production method of the present invention may produce granules by injecting an organic-inorganic composite solution having a different composition according to the use thereof into a predetermined micro-granule coater. Accordingly, there is an advantage in that it is easy to produce organic-inorganic spherical granules having suitable conditions for the production of ceramic granules without expertise in a micro-granule coater.

DESCRIPTION OF DRAWINGS

FIGS. 1A, 1B, 1C, and 1D are views showing the photograph, size, and size distribution of composite granules produced according to embodiments of the present invention;

FIGS. 2A, 2B, and 2C are views showing the drug release properties of composite granules produced according to embodiments of the present invention;

FIGS. 3A and 3B are views showing the cell proliferation behavior by composite granules produced according to embodiments of the present invention;

FIG. 4 is a view showing the cell delivery capacity of composite granules produced according to embodiments of the present invention;

FIGS. 5A and 5B are photographs showing the degree of dispersion of an inorganic member in an organic member according to a mixing method;

FIGS. 6A and 6B are photographs and graphs showing the shape, size, and size distribution of organic-inorganic composite granules produced according to embodiments of the present invention;

FIG. 7 is a step diagram of a method for producing ceramic granules according to an embodiment of the present invention;

FIG. 8 shows spherical ceramic granules produced according to an embodiment of the present invention; and FIGS. 9 to 30B show data for an embodiment of the present invention.

DETAILED DESCRIPTION

Hereinafter, the present invention will be described in detail with reference to the contents described in accompanying drawings. However, the present invention is not limited or restricted to exemplary embodiments. Like reference numeral shown in each drawing denote members performing substantially the same function.

Objects and effects of the present invention may be naturally understood or more apparent by the description below. However, the objects and effects of the present invention are not limited to the following description. In addition, in describing the present invention, when it is determined that detailed descriptions of known technologies related to the present invention may unnecessarily obscure the gist of the present invention, the detailed descriptions will be omitted.

In the present invention, a 'size' means a diameter when an object is in a spherical shape, and means the length of a long axis when the object is in an oval shape.

The present invention includes an organic member and an inorganic member, wherein the inorganic member has a weight ratio of 1 to 10 to the organic member, a size of 100-2000 μm, a size distribution in the range of −20% to +20% to the size of granules, and is a hydrogel phase. Hereinafter, organic-inorganic composite granules according to the present invention will be described in detail for each component.

The organic-inorganic composite granules according to the present invention includes an organic member and an inorganic member. At this time, the organic member may be a natural biopolymer or a synthetic biopolymer. Specifically, the organic member may be at least one among alginate, collagen, gelatin, chitosan, cellulose, hyaluronate, and a biopolymer, or may be a combination thereof. Also, the inorganic member of the present invention may be a ceramic member. Specifically, the inorganic member may be any one of a calcium phosphate-based member, a bioglass-based member, an alumina-based member, a zirconia-based member, and a composite thereof. The calcium phosphate-based member may be any one of hydroxy apatite (HA), dicalcium phosphate (DCP), tricalcium phosphate (TCP), tetracalcium phosphate (TTCP), and octacalcium phosphate (OCP), but is not limited thereto.

The organic-inorganic composite granules according to the present invention have a structure in which an inorganic member is uniformly dispersed in an organic member, so that the size of the composite granules may be uniform. In addition, there is an effect of greatly improving the utility of the organic-inorganic composite granules, such as the sustained release properties of a functional member and the effective culture of cells, which are to be added.

Specifically, when granules are produced only with an organic member or an inorganic member, there is a problem in that it is difficult to perform a function as a carrier of the functional member due to the immediate release properties of the granules. In addition, when granules are produced only with an inorganic member, cells may not be cultured or transferred on the granules, so that there is a limitation in applying the same to, for example, a medical field. The organic-inorganic composite granules according to the present invention have sustained release properties when a functional member is supported therein, and also has an advantage in that the application field thereof may be greatly expanded by enabling the culture and delivery of cells.

At this time, the organic-inorganic composite granules of the present invention has a weight ratio of the inorganic member to the organic member of 1 to 10, preferably 5 to 10. The present invention has an advantage in that the sustained release properties of granules are further improved by including a large amount of the inorganic member in the granules, and also has an advantage in that relatively a large amount of bone forming components are included when the granules are used as a bone filler and the like. For example, when the weight ratio of the inorganic member is less than 1, the effect of improving the sustained release properties of the granules may be insignificant, and when used as a bone filler and the like, there may be a problem in that there are not enough bone forming components. Also, when the weight ratio of the inorganic member is greater than 10, it may be difficult to form granules having uniform properties due to a problem such as the agglomeration of the inorganic member.

The size of the organic-inorganic composite granules according to the present invention is 100-2000 µm, and the size distribution thereof ranges from −20% to +20% based on the size of the granules. The organic-inorganic composite granules according to the present invention have a size range and a size distribution range as described above, and thus, have excellent specification stability and very good ease of application for a variety of applications.

In addition, the organic-inorganic composite granules according to the present invention are in a hydrogel phase. Accordingly, the composite granules of the present invention are advantageous in delivering bioactive substances such as cells, drugs, and proteins compared to granules in a simple solid phase. Also, the composite granules of the present invention are advantageous in maintaining the viability of cells and delivering the bioactive substances to the inside of a human body, and are expected to have a higher supporting efficiency of drugs and the like than granules in a simple solid phase. In addition, the organic-inorganic composite granules of the present invention which are in a hydrogel phase are advantageous in adjusting/controlling a drug release behavior to be sustained release compared to granules in a simple solid phase. In order to support a drug or a protein, granules in a simple solid phase are adsorbed to the surface of granules in a solid phase and delivered. This is because after the delivery, the surface on which the drug or the protein is supported is directly exposed to a portion to be delivered, so that there is a phenomenon in which an initial excess is released, and it is difficult to control the release behavior for a long period time thereafter. On the other hand, in the case of the composite granules in a hydrogel phase, since an inorganic member supported with drugs and the like are supported in a hydrogel and delivered, it is possible to reduce a phenomenon in which an initial excess is release and control the release behavior using the physical/chemical properties of the hydrogel. Also, in the case of the composite granules in a hydrogel phase, cells or drugs may be delivered in a hydrogel so that two functional drugs or a protein such as a growth factor may be simultaneously delivered and the sequential release behavior thereof may be implemented. In addition, in order to deliver granules in a solid phase to the inside of a human body, the granules must be delivered through a surgical procedure which exposes a portion to be delivered to the outside, or mixed with other carriers in a hydrogel phase and then delivered through a syringe. However, the composite granules in a hydrogel phase have an advantage in that the granules may be delivered through a non-invasive method.

The organic-inorganic composite granules according to the present invention may further include a functional member or a cell. In this case, the functional member is an object to be supported in the organic-inorganic composite granules and delivered, and may be bisphosphonate-based drug, a polyphenolic natural-derived substance, and the like.

More specifically, the functional member may include one or more materials selected from the group consisting of alendronate, risedronate, etidronate, clodronate, neridronate, ibandronate, zoledronate, and olpadronate, which are bisphosphonate-based drugs used as bone absorption inhibitors.

In addition, the functional member may include one or more materials selected from the group consisting of quercetein, genistein, curcumin, saurolactam, sauchinone, baicalin, daidzein, rutin, anthocyanidin, fisetin, icariin, kaempferol, *E. koreanum* nakei, and Equol, which are polyphenolic natural-derived substances.

The functional member is not limited to the above materials and may be selected and applied depending on the functionality required.

The functional member may be an organic material or an inorganic material. Particularly, cells, tissues, hormones and growth factors such as BMP that may induce the generation of bone tissues as a bone formation promoter, and the like are included in the functional member, so that it is possible to promote bone formation since the release of the functional member occurs for a target cell in a body.

When the organic-inorganic composite granules according to the present invention include cells, stem cells, for example, may be cultured on the organic-inorganic composite granules of the present invention, and then delivered to the inside of a body.

The organic-inorganic composite granules according to the present invention may not include a dispersant. The organic-inorganic composite granules according to the present invention may be used in a pharmaceutical field, a medical field, a cosmetics field, a food field, and the like. In this case, when the granules include a chemical substance such as a dispersant, there may be a limitation in the application. Considering the above, the organic-inorganic composite granules according to the present invention may not include a dispersant, especially when used in the above fields and the like. Examples of the application of the organic-inorganic composite granules according to the present invention may include a bone filler, a bone graft, and a filler. The granules may be used as a replacement in a field in which a bone filler supported on spongy bone pores and inducing the promotion of bone formation, a cosmetic and molding filler material, and a fine plastic material are used.

Also, the present invention provides a method for producing granules, the method characterized by including preparing an organic member solution, uniformly dispersing an inorganic member in the organic member solution at a weight ratio of 1 to 10 based on an organic member to form an organic-inorganic composite solution, spraying the organic-inorganic composite solution in an electrostatic charge manner, and polymerizing the sprayed organic-inorganic composite solution to form a hydrogel phase.

Hereinafter, each step of the production method of the present invention will be described in detail.

The production method of the present invention includes preparing an organic member solution. At this time, the organic member may be a natural biopolymer or a synthetic biopolymer. Specifically, the organic member may be at least one among alginate, collagen, gelatin, chitosan, cellulose, hyaluronate, and a biopolymer, or may be a combination thereof.

The organic member is dissolved in, for example, a phosphate buffer saline to prepare an organic member solution. Alternatively, the organic member may be dissolved and dispersed in water, glycerin, lipid oil, and the like.

At this time, it is preferable that an organic solvent is not used in preparing an organic member solution of the production method of the present invention. When an organic solvent is used in the production process, due to a problem such as cytotoxicity, there may be a limitation in using a resultant in a medical field. Therefore, in the production method of the present invention, an organic solvent is not used to prevent a problem which may occur in applying the composite granules according to the present invention to pharmaceutical, medical, food, or cosmetics fields.

Next, the production method of the present invention includes uniformly dispersing an inorganic member in the organic member solution at a weight ratio of 1 to 10 based on an organic member to form an organic-inorganic composite solution.

The inorganic member dispersed in the above step may be a ceramic member. Specifically, the inorganic member may be any one of a calcium phosphate-based member, a bioglass-based member, an alumina-based member, a zirconia-based member, and a composite thereof. The calcium phosphate-based member may be any one of hydroxy apatite (HA), dicalcium phosphate (DCP), tricalcium phosphate (TCP), tetracalcium phosphate (TTCP), and octacalcium phosphate (OCP), but is not limited thereto.

At this time, the inorganic member dispersed in the production method of the present invention may include a functional member. The functional member may be included in the inorganic member by various methods such as adsorption. Specific examples of the functional member may include, as described above, a bisphosphonate-based drug, a polyphenolic natural-derived material, and the like.

In the production method of the present invention, an inorganic member is introduced in the organic member solution at a weight ratio of 1 to 10 based on the organic member, preferably, at a weight ratio of 5 to 10. The present invention has an advantage in that the sustained release properties of granules are further improved by including a large amount of the inorganic member in the composite solution, and also has an advantage in that relatively a large amount of bone forming components are included when the granules are used as a bone filler and the like. For example, when the weight ratio of the inorganic member is less than 1, the effect of improving the sustained release properties of the granules may be insignificant, and when used as a bone filler and the like, there may be a problem in that there are not enough bone forming components. Also, when the weight ratio of the inorganic member is greater than 10, a problem may occur in the step of forming granules due to a problem such as the aggregation of the inorganic member, nozzle clogging, and the like, so that it may be difficult to form granules having uniform properties.

Meanwhile, the inorganic member has strong cohesiveness and very low dispersibility, so that it is necessary that the inorganic member is introduced while being uniformly dispersed in an organic member solution. For example, for such dispersion, it is preferable that the production method of the present invention further includes, after forming the organic-inorganic composite solution as described above, dispersing the inorganic member with a rotation and revolution mixer and stirring the resultant composite solution with an ultrasonic mixer.

As described below, the production method of the present invention forms granules by spraying in an electrostatic manner. The electrostatic charge method has an advantage of producing granules having a relatively uniform size. However, there may be a problem in that a nozzle is clogged during a process, making it impossible to produce granules. Particularly, when an organic-inorganic composite solution containing an inorganic member having a very high cohesiveness as in the present invention is used as a raw material, a nozzle is very easily clogged due to the aggregation of the inorganic member in the raw material. Therefore, it is not easy to consider making granules by spraying a raw material containing an inorganic member in an electrostatic charge manner.

In order to solve the above problem, in the present invention, it is preferable to further include dispersing the inorganic member with a rotation and revolution mixer and stirring the resultant composite solution with an ultrasonic mixer as described above for the organic-inorganic composite solution formed from a raw material by electrostatic charge spraying. Through the above process, it is possible to prevent the nozzle from being clogged and produce granule having uniform physical properties.

However, when the rotation and revolution mixer and the ultrasonic mixer are used for an excessive amount of time, the temperature of the composite solution is greatly increased, which may cause a problem when the composite solution contains a functional member or cells. That is, when the temperature of the composite solution is excessively increased, there is a problem in that the properties of a drug which may be included therein may change, or the cells may die. When considering the above, it is preferable that mixing using a rotation and revolution mixer and an ultrasonic mixer is performed in a range in which the temperature of the composite solution does not exceed 40° C. For example, mixing using the rotation and revolution may be performed within 6 minutes, and mixing using the ultrasonic mixer may be performed within 30 minutes.

Meanwhile, a step of supporting a functional member or cells in the organic-inorganic composite solution formed in the production method of the present invention may be further included. As described above, the functional member may be mixed with the organic member solution while being contained in the inorganic member, or may be included after the organic-inorganic composite solution is prepared. When the organic-inorganic composite solution supports the functional member or the cells, it is necessary to adjust the process conditions so as not to adversely affect the supported functional member or the cells when using the rotation and revolution mixer or the ultrasonic mixer as described above.

Next, the production method of the present invention includes spraying the organic-inorganic composite solution in an electrostatic charge manner. For example, the spraying in an electrostatic charge manner may be performed using a micro-granule coater. When granules are produced by an electrostatic charge method, there are advantages in that the yield is excellent since most of the raw materials introduced may be converted into granules, a large amount of granules may be produced in a short time, and granules may be produced in a relatively uniform size. However, there is a problem in that a nozzle may be clogged when the viscosity or degree of aggregation of a raw material is high. The organic member included in the raw material used in the production method of the present invention has a high viscosity, and the inorganic member included in the raw material has a very high cohesiveness, and thus, are not suitable for making granules in an electrostatic manner. However, by uniformly dispersing the inorganic member in the organic member solution when forming the organic-inorganic composite solution, and additionally, if necessary, by adding a step of dispersing the inorganic member with a rotation and revolution mixer and stirring the resultant composite solution with an ultrasonic mixer, it is possible to produce granules by an electrostatic charge method.

When the above step is performed with a micro-granule coater, the size of a spray nozzle of the micro-granule coater is preferably 50 μm to 1000 μm. When the size is less than 50 μm, there is a problem in that it is difficult to spray the organic-inorganic composition solution containing the inorganic member through the nozzle due to a problem such as nozzle clogging. When the size is greater than 1000 μm, there is a problem in that it is difficult to produce micro-sized particles which are easy to be applied to current clinical applications. In addition, the voltage is preferably 500 V to 2,500 V. When the voltage is less than 500 V, there is a problem in that it is difficult to produce spherical particles since it is difficult to uniformly spray a solution to be sprayed. When the voltage is greater than 2,500 V, there is a problem in that it is difficult to produce granules at a high yield since a solution formed in a spherical shape is sprayed in an excessively expanded form after the spraying. Also, the pressure is preferably 100 mbar to 1500 mbar. When the pressure is less than 100 mbar, a nozzle is frequently clogged and there is a problem in that a solution passed through the nozzle is excessively wide spread. When the pressure is greater than 1500 mbar, a solution formed in a spherical shape is applied with greater force than necessary when being dropped into a polymerization-inducing solution (for example a $CaCl_2$) solution), so that it is difficult to form spherical granules. Furthermore, the vibration frequency is preferably 100 Hz to 6,000 Hz. When the vibration frequency is greater than 6,000 Hz, there is a problem in that spherical granules with tails are formed.

The production method according to the present invention includes polymerizing the organic-inorganic composite solution sprayed by the above method to form a hydrogel phase. The polymerization may be performed by any one of ion crosslinking, chemical crosslinking, and photo crosslinking. Among the above, the ion crosslinking may be performed using at least one polymerization-inducing material among calcium chloride ($CaCl_2$)), calcium sulfate ($CaSO_4$), and calcium carbonate ($CaSO_4$). Specifically, the step may be performed by dropping the sprayed organic-inorganic composite solution to a $CaCl_2$) polymerization-inducing solution. According to the production method of the present invention, since the granules are formed in a hydrogel phase, not in a simple solid, it is advantageous in delivering bioactive substances such as cells, drugs, and proteins when compared with granules in a simple solid phase. Also, the granules of the present invention are advantageous in maintaining the viability of cells and delivering the same to the inside of a human body, and are expected to have a higher supporting efficiency of drugs and the like than granules in a simple solid phase. In addition, the organic-inorganic composite granules of the present invention which are in a hydrogel phase are advantageous in adjusting/controlling a drug release behavior to be sustained release compared to granules in a simple solid phase. In order to support a drug or a protein, granules in a simple solid phase are adsorbed to the surface of granules in a solid phase and delivered. This is because after the delivery, the surface on which the drug or the protein is supported is directly exposed to a portion to be delivered, so that there is a phenomenon in which an initial excess is released, and it is difficult to control the release behavior for a long period time thereafter. On the other hand, in the case of the composite granules in a hydrogel phase, since an inorganic member supported with drugs and the like are supported in a hydrogel and delivered, it is possible to reduce a phenomenon in which an initial excess is release and control the release behavior using the physical/chemical properties of the hydrogel. Also, in the case of the composite granules in a hydrogel phase, cells or drugs may be delivered in a hydrogel so that two functional drugs or a protein such as a growth factor may be simultaneously delivered and the sequential release behavior thereof may be implemented. In addition, in order to deliver granules in a solid phase to the inside of a human body, the granules must be delivered through a surgical procedure which exposes a portion to be delivered to the outside, or mixed with other carriers in a hydrogel phase and then delivered through a syringe. However, the composite granules in a hydrogel phase have an advantage in that the granules may be delivered through a non-invasive method.

The concentration of an organic member solution used in the production method of the present invention is preferably 0.5-2.0 wt %. When the concentration is less than 0.5 wt %, the concentration of the organic member is too low to achieve a sufficient crosslinking density, so that there is a problem in that it is difficult to maintain sufficient mechanical properties of the produced granules. When the concentration is greater than 2.0 wt %, the concentration is too high, so that a solution having a high viscosity is formed, making it difficult to uniformly disperse the composite solution, and thus, there is a problem in that it is difficult to form droplets in a uniform spherical shape using spraying equipment.

Also, the size of the inorganic member used in the production method of the present invention is preferably in the range of 50 nm to 50 μm. When the size is less than 50 nm, the surface area of the inorganic member (for example, ceramic powder) is increased, so that the inorganic member may not be uniformly dispersed in the inorganic member (for example, alginate solution), and there is a chance that the inorganic member may be discharged to the outside through pores inside a hydrogel. In addition, in the case in which cells are supported, there is a problem of endocytosis, which cannot be ignored. When the size is greater than 50 μm, it is difficult for the inorganic member to pass through a micro-sized nozzle, so that there is a problem in that it is difficult to produce particles.

In the production method of the present invention, it is preferable that a dispersant for dispersing the inorganic member is not used. In general, a dispersant is used for uniform dispersion due to the cohesiveness of an inorganic member. When a dispersant is included in granules to be produced, there may be a problem in applying the same, for example, to medical, pharmaceutical, food, and cosmetics fields. Accordingly, since a dispersant is not used in the production method of the present invention, there is an advantage in that the fields of application of the granules to be produced may be greatly expanded. In the production method of the present invention, instead of using a dispersant, stirring and dispersion are performed using a rotation and revolution mixer or an ultrasonic mixer for the uniform dispersion of the inorganic member.

According to the production method of the present invention, in producing granules having sustained release properties and cell delivery properties, especially organic-inorganic composite granules, the granules are produced in an electrostatic charge manner, so that there are advantages in that the yield is improved and a large amount of granules may be produced in a short time. In addition, granules having a uniform size may be produced, so that there is an advantage in that the granules may be applied to various fields. In addition, since a functional member or a cell may be easily supported and there is no need to use an organic solvent or a dispersant in the production process, there is an advantage in that the application field of the granules may be greatly expanded to medical, pharmaceutical, food, and cosmetics fields.

Also, the present invention provides a method for producing granules, the method characterized by further including preparing an organic member solution, a) uniformly dispersing an inorganic member in the organic member solution at a weight ratio of 1 to 10 based on an organic member to form an organic-inorganic composite solution, b) spraying the organic-inorganic composite solution in an electrostatic charge manner, c) polymerizing the sprayed organic-inorganic composite solution to form a hydrogel phase, d) washing and drying the hydrogel phase formed through the above step, and e) sintering the washed and dried hydrogel phase.

FIG. 7 is a step diagram of a method for producing granules according to an embodiment of the present invention, especially ceramic granules. Referring to FIG. 7, the method for producing ceramic granules includes a) preparing an organic-inorganic composite solution S1, b) spraying the organic-inorganic composite solution prepared in Step a) in an electrostatic charge manner S3, c) polymerizing the organic-inorganic composite solution sprayed in Step b) to form a hydrogel phase S5, d) washing and drying the hydrogel phase formed in Step c) S7, and e) sintering the hydrogel phase washed and dried in Step d) to form granules S9.

The step of preparing an organic member solution is the same as described above, and thus, the description thereof will be omitted.

In Step a) S1, an organic-inorganic composite solution suitable for experimental conditions may be prepared by purchasing, producing, and the like. Hereinafter, the method for preparing an organic-inorganic composite solution performed in Step a) S1 will be described.

In order to prepare the organic-inorganic composite solution of Step a) S1, a solution containing an organic member in a solvent may be prepared. The organic member may be at least one among alginate, collagen, gelatin, chitosan, cellulose, hyaluronate, and a biopolymer, or may be a combination thereof. The solvent is commonly used in dispersing an organic member, and may be any one of water, glycerin, and lipid oil. In the solution containing the organic member, the content of the organic member may be 0.5-5 wt %. The content of the organic member may be 1-2 wt %.

Next, the solution containing the organic member may be mixed with an inorganic member. The inorganic member may have an average diameter of 20 nm to 10 μm. The inorganic member may have an average diameter of 20-100 nm. The inorganic member may be any one of a calcium phosphate-based member, a bioglass-based member, an alumina-based member, a zirconia-based member, and a composite thereof. The calcium phosphate-based member may be any one of hydroxy apatite (HA), dicalcium phosphate (DCP), tricalcium phosphate (TCP), tetracalcium phosphate (TTCP), and octacalcium phosphate (OCP), but is not limited thereto.

In order to evenly disperse the inorganic member in the solution in which the organic member is dispersed, the inorganic member may be introduced into the solution in which the organic member is dispersed using powder. Also, the inorganic member may be dispersed through a dispersion apparatus. At this time, the introduction using powder and the dispersion using a dispersion apparatus may be simultaneously performed to increase a dispersion rate. The dispersion apparatus may be an ultrasonic dispersion apparatus. The dispersion process may be performed under a suitable time and suitable conditions to evenly disperse the inorganic member in the solution in which the organic member is dispersed. The process may be understood as an important factor for preventing the deterioration of yield caused by a nozzle clogging phenomenon in the production of granules using a micro-granule coater.

Meanwhile, depending on the content of the inorganic member introduced to the solution containing the organic member, the shrinkage rate of granules may be different, through which it is possible to control the size of the granules by controlling the production conditions of the granules other than the process conditions of the micro-granule coater.

Next, in Step a) S1, the solution containing the organic member and the inorganic member is stirred to prevent the organic member and the inorganic member from being agglomerated. The stirring may be performed using an ultrasonic mixer. The stirring process may be performed under a suitable time and suitable conditions to prevent the organic member and the inorganic member from being agglomerated. Particularly, the Step a) S1 may include a step of setting the content of an inorganic matter for an organic matter. Through the above, the size and porosity of granules produced through the following process may be controlled.

In Step b) S3, spherical granules of a desired size may be produced in an electrostatic charge manner, for example, using a micro-granule coater. In Step b) S3, the average diameter of the granules may be controlled according to the change in the spray nozzle size, pneumatic conditions, and frequency of the micro-granule coater. By going though Step b) S3, spherical granules having an average diameter value preferably formed in the range of 40-2000 μm may be produced.

Particularly, Step b) S3 may include injecting the organic-inorganic composite solution prepared in Step a) S1, and spraying the organic-inorganic composite solution into an electric field through a nozzle of the micro-granule coater to form spherical granules.

The micro-granule coater used in Step b) S3 is a device for making a solution into granules in a droplet shape. By spraying a solution from a nozzle and by applying vibration to the nozzle and the solution, the micro-granule coater may allow granules in a droplet shape and having a predetermined size to be formed and separated, and by applying electrostatic charge to the granules in a droplet shape, the micro-granule coater may allow the granules to be dispersed and separated. A container containing a solution may be placed in a lower portion of the nozzle, the granules may be dropped into the solution in the container.

For example, the micro-granule coater may include a nozzle through which a solution is sprayed, a pump for supplying the solution to the nozzle, a vibrator for applying vibration to the nozzle to allow the solution sprayed from the nozzle to form granules in a droplet shape, and an electrostatic charge for applying electrostatic charge to disperse the formed granules in a droplet shape. In an embodiment of the present invention, Encapsulator B-395 Pro manufactured by Buchi was used as the micro-granule coater.

The method for producing granules according to an embodiment of the present invention uses a micro-granule coater, so that the uniformity of the size of granules is improved and the size and shape of the granules may be controlled.

In Step c) S5, a polymerization reaction of the organic member contained in the granules produced in Step b) S3 is induced to maintain the form of a spherical shape as a hydrogel phase. To this end, a polymerization-inducing material may be added to a solution supported with the granules produced from the micro-granule coater. More preferably, granular droplets sprayed from the micro-granule coater may be directly dropped to a solution containing a polymerization-inducing material. Through the above, the formation of granules and the polymerization reaction may occur simultaneously, so that the shape and size of the granules produced by the polymerization may be more efficiently controlled, and the polymerization reaction may be allowed to occur in the state in which the dispersibility of the granules dispersed due to the electrostatic charge applied from the micro-granule coater is high, so that the size of the granules generated by the polymerization may be uniformly controlled.

At this time, the concentration of the solution containing the polymerization-inducing material may be 50-300 mM, and may be 100 mM. The polymerization-inducing material may be understood as a material capable of inducing a polymerization reaction of organic-inorganic granules to grow the granules sprayed from the micro-granule coater and supported. In addition, in general, polymerization induction may use ion crosslinking using divalent cations such as calcium chloride ($CaCl_2$)), calcium sulfate ($CaSO_4$), calcium carbonate ($CaCO_3$), chemical crosslinking using chemical substances such as alginate, collagen, gelatin, hyaluronate, and N-(3-Dimethylaminopropyl)-N'-ethylcarbodiimide (EDC), Glutaraldehyde, Adipic acid dihydrazide (ADH), genipin, which are available for water-soluble polymer crosslinking, and photo crosslinking polymerizing a water-soluble polymer material incorporating an acrylate group or a methacrylate group using ultraviolet (UV) rays. The solvent of the solution containing the polymerization-inducing material may be any one of water, methanol, ethanol, isopropanol, glycerin, polyethylene glycol, and lipid oil.

In Step d) S7, the granules in a hydrogel phase polymerized in Step c) S5 are washed and dried. In Step d) S7, the polymerized granules may be stabilized for 30 minutes to 2 hours, and then a washing process for removing unreacted components remaining in the granules may be performed. The stabilizing and washing may be performed using a phosphate buffer saline (PBS). Consequently, a process for drying the washed granules may be performed. The drying process may be performed by leaving the granules for a sufficient amount of time at room temperature, or may be performed using a dryer. At this time, the drying conditions may be a pressure below atmospheric pressure ($1 \times 10^{-5}$ Pa to $1 \times 10^5$ Pa) and a temperature above room temperature (0° C. to 60° C.), but are not particularly limited.

In Step e) S9, sintering of the granules in a hydrogel phase which were washed and dried in Step d) S7 is performed. The sintering may be performed at a temperature of 500° C. to 1500° C. depending on the type of the organic member and the inorganic member included in the granules, and may be preferably performed at a temperature of 1000° C. to 1300° C. Through the sintering process, ceramic beads in the form of granulated particles from which an organic matter has been removed may be formed. That is, in Step e) S9, organic matters are removed through sintering, so that granules, especially spherical ceramic granules may be stabilized.

Granules produced through the sintering process, especially ceramic granules include a ceramic composition including pores and calcium oxide (CaO) included in the ceramic composition. The calcium oxide (CaO) is derived from the polymerization-inducing material described above. The method for producing ceramic granules according to an embodiment of the present invention has an advantage in that ceramic granules are produced at a high yield since the ceramic granules are produced through a series of processes described above, and has an advantage in that a large amount of granules may be produced in a short time by using a micro-granule coater in an electrostatic charge manner. In addition, by performing the polymerization process separately from the granule production process by a micro-granule coater, ceramic granules having a uniform size may be produced.

Meanwhile, the inorganic member has strong cohesiveness and very low dispersibility, so that it is necessary that the inorganic member is introduced while being uniformly dispersed in an organic member solution. For example, for such dispersion, it is preferable that the production method of the present invention further includes, after forming the organic-inorganic composite solution as described above, stirring the same with an ultrasonic mixer and then dispersing the inorganic member with a rotation and revolution mixer.

The production method of the present invention forms granules by spraying in an electrostatic manner. The electrostatic charge method has an advantage of producing granules having a relatively uniform size. However, there may be a problem in that a nozzle is clogged during a process, making it impossible to produce granules. Particularly, when an organic-inorganic composite solution containing an inorganic member having a very high cohesiveness as in the present invention is used as a raw material, a nozzle is easily clogged due to the aggregation of the inorganic member in the raw material. Therefore, it is not easy to consider making granules by spraying a raw material containing an inorganic member in an electrostatic charge manner.

In order to solve the above problem, in the present invention, it is preferable to further include stirring the organic-inorganic composite solution formed of the raw material of the electrostatic charge spraying with an ultrasonic mixer as described above, and dispersing the inorganic member with a rotation and revolution mixer. Through the above process, it is possible to prevent the nozzle from being clogged and produce granule having uniform physical properties.

In the production method of the present invention, it is preferable that a dispersant for dispersing the inorganic member is not used. In general, a dispersant is used for uniform dispersion due to the cohesiveness of an inorganic member. When a dispersant is included in granules to be produced, there may be a problem in applying the same, for example, to medical, pharmaceutical, food, and cosmetics fields. Accordingly, since a dispersant is not used in the production method of the present invention, there is an advantage in that the fields of application of the granules to be produced may be greatly expanded. In the production method of the present invention, instead of using a dispersant, stirring and dispersion are performed using an ultrasonic mixer or a rotation and revolution mixer for the uniform dispersion of the inorganic member.

FIG. 8 shows ceramic granules produced according to an embodiment of the present invention. FIG. 8 is an enlarged view of the ceramic granules by 500 times, and the ceramic granules may have a shape close to a spherical shape. Also, the surfaces of the ceramic granules may vary in roughness for each portion, pores may be formed and distributed on the surfaces.

Meanwhile, the ceramic granules produced according to the present embodiment may have a different shrinkage rate of ceramic granules according to the content of an organic matter and an inorganic matter. In addition, the ceramic granules may have a controlled porosity of sintered ceramic granules according to the content of the organic and inorganic materials.

Meanwhile, spherical ceramic granules produced according to an embodiment of the present invention may be used for a bone filler. In addition, spherical ceramic granules produced according to an embodiment of the present invention may be used as a replacement in a field in which a bone filler supported on spongy bone pores and inducing the promotion of bone formation, a cosmetic and molding filler material, and a fine plastic material are used in addition to pharmaceutical, cosmetics, and food fields.

Hereinafter, the present invention will be described in more detail based on Examples, Comparative Examples, and Experimental Examples. The following Examples, Comparative Examples, and Experimental Examples are merely illustrative of the present invention, and the scope of the present invention is not limited to the following description.

Best Mode

In Examples 1 to 16, Comparative Example 1, and Experimental Examples 1 to 7 below, since a process of uniformly dispersing an inorganic member in an organic solution is the most important when granules are produced in an electrostatic charge manner using a micro-sized nozzle, organic-inorganic composite granules were produced by maximally dispersing the inorganic member using a rotation and revolution mixer and an ultrasonic mixer. Even though the time for using the rotation and revolution mixer was increased, the degree of dispersion was not greatly improved, and there was a risk of denaturation due to heat as an organic matter was used. Therefore, the time for using the rotation and revolution mixer was fixed to 6 minutes or less. Thereafter, mixing was performed using the ultrasonic mixer. Although the degree of dispersion was greatly increased according to the mixing time, when the ultrasonic mixer treatment time passed 30 minutes, the temperature in the solution reached about 40° C. Therefore, after the treatment, the delivery of bioactive substances such as cells and proteins may be constrained, so that the ultrasonic mixer treatment time was limited to within 30 minutes.

Example 1

Alginate, which is an organic member, was dissolved in tertiary distilled water to prepare a 1.0 wt % alginate solution, and nano-apatite, which is an inorganic member, was mixed thereto at a weight ratio of 1:1 (organic member: inorganic member) using a rotation and revolution mixer and an ultrasonic mixer to prepare an organic-inorganic composite solution. At this time, a paste mixer was used as the rotation and revolution mixer, and a rotational sonicator was used as the ultrasonic mixer. The mixing using each thereof was performed for 6 minutes and 15 minutes, respectively.

The prepared organic-inorganic composite solution was introduced into a micro-granule coater (trade name: B-395 pro, manufactured by Buchi) to be sprayed using a nozzle having a diameter of 150 μm, and then the sprayed organic-inorganic composite solution was dropped to a $CaCl_2$) solution to prepare organic-inorganic composite granules in a hydrogel phase. After the dropping, stirring was performed in the $CaCl_2$) solution for 30 minutes, and then washing was performed two times with PBS. Thereafter, in order to measure the size of granules, a predetermined amount of organic/inorganic composite granules were transferred to a petri dish to obtain an image through an optical microscope. The size of the granules was determined by analyzing the image using a program called ImageJ and then calculating the average size of the granules.

Example 2

Organic-inorganic composite granules in a hydrogel phase were produced in the same manner as in Example 1 except that quercetin, which is a functional member, was mixed with the organic-inorganic composite solution in an amount of 1 wt % based on the weight of the organic-inorganic composite solution.

Example 3

Organic-inorganic composite granules in a hydrogel phase were produced in the same manner as in Example 1 except that quercetin, which is a functional member, was mixed with the organic-inorganic composite solution in an amount of 2.5 wt % based on the weight of the organic-inorganic composite solution.

Example 4

Organic-inorganic composite granules in a hydrogel phase were produced in the same manner as in Example 1 except that quercetin, which is a functional member, was mixed with the organic-inorganic composite solution in an amount of 5 wt % based on the weight of the organic-inorganic composite solution.

Example 5

Alginate, which is an organic member, was dissolved in tertiary distilled water to prepare a 1.0 wt % alginate solution, and nano-apatite, which is an inorganic member, was mixed thereto at a weight ratio of 1:4 (organic member: inorganic member) using a rotation and revolution mixer and an ultrasonic mixer to prepare an organic-inorganic composite solution. At this time, a paste mixer was used as the rotation and revolution mixer, and a rotational sonicator was used as the ultrasonic mixer. The mixing using each thereof was performed for 6 minutes and 15 minutes, respectively.

The prepared organic-inorganic composite solution was introduced into a micro-granule coater (trade name: B-395 pro, manufactured by Buchi) to be sprayed using a nozzle having a diameter of 150 μm, and then the sprayed organic-inorganic composite solution was dropped to a CaCl$_2$) solution to prepare organic-inorganic composite granules in a hydrogel phase. After the dropping, stirring was performed in the CaCl$_2$) solution for 30 minutes, and then washing was performed two times with PBS. Thereafter, in order to measure the size of granules, a predetermined amount of organic/inorganic composite granules were transferred to a petri dish to obtain an image through an optical microscope. The size of the granules was determined by analyzing the image using a program called ImageJ and then calculating the average size of the granules.

Example 6

Organic-inorganic composite granules were produced in the same manner as in Example 5 except that the ratio of the organic member:inorganic member was 1:6.

Example 7

Organic-inorganic composite granules were produced in the same manner as in Example 5 except that the ratio of the organic member:inorganic member was 1:8.

Example 8

Organic-inorganic composite granules were produced in the same manner as in Example 5 except that the ratio of the organic member:inorganic member was 1:10.

Examples 9 to 12

Organic-inorganic composite granules were produced in the same manner as in Examples 5 to 8 except that a nozzle having a diameter of 120 μm was used.

Examples 13 to 16

Organic-inorganic composite granules were produced in the same manner as in Examples 5 to 8 except that a nozzle having a diameter of 200 μm was used.

Comparative Example 1

An experiment was conducted to produce organic-inorganic composite granules in the same manner as in Example 1 except that nano-apatite, which is an inorganic member, was mixed at a weight ratio of 1:20 (organic member: inorganic member).

However, during the process, nozzle clogging of the micro-granule coater was severe and the ceramic content in the granules produced was significantly lower than the theoretical content, so that it was impossible to produce uniform granules, thereby confirming that the production yield was significantly reduced.

Experimental Example 1

Identification of Composite Granule Size

In order to identify the size and size distribution of the organic-inorganic composite granules produced according to the present invention, an experiment was conducted as follows.

The form of granules was confirmed through an optical microscope for the organic-inorganic composite granules produced in each of Example 1 to Example 4, and the size and size distribution each thereof was confirmed using the ImageJ software. The results are shown in FIG. 1A to FIG. 1D.

Referring to FIG. 1A to FIG. 1D, the organic-inorganic composite granules according to the present invention are in a spherical shape, have a size in the range of about 250-270 μm, and have a size distribution not deviating from ±20%, thereby having a uniform size.

Experimental Example 2

Identification of Supporting Amount of Inorganic Member

In order to identify the supporting amount of the inorganic member in the organic-inorganic composite granules produced, an experiment was conducted as follows.

The weight ratio of the actual organic member and the inorganic member was measured for the organic-inorganic composite granules produced in the same manner as in Example 1 except that the content of the organic member and the inorganic member was adjusted as shown in Table 1 below.

TABLE 1

| Organic member:Inorganic member | Theoretical weight ratio | Actual weight ratio |
|---|---|---|
| 1:0.1 | 0.1 | 0.124 |
| 1:0.25 | 0.25 | 0.271 |
| 1:1 | 1 | 0.962 |
| 1:2.5 | 2.5 | 2.796 |
| 1:10 | 10 | 7.760 |

According to Table 1, the inorganic member content of the organic-inorganic composite granules actually produced is almost the same as the amount of the inorganic member introduced into the raw material, so that it was confirmed that the composite granules were produced in a high yield without the precipitation or clogging of the inorganic member in the manufacturing process.

Experimental Example 3

Identification of Drug Sustained Release Properties

In order to identify the drug sustained release properties of the organic-inorganic composite granules of the present invention, an experiment was conducted as follows.

The organic-inorganic complex granules produced in each of Examples 1 to 4 of the present invention were placed on MC3T3 osteoblasts as shown in FIG. 2B, and the amount of drug released over time and the degree of proliferation of cells over time were measured. The results are shown in FIG. 2A and FIG. 2C, respectively.

The organic-inorganic composite granules prepared in each of Examples 1 to 4 were introduced into a phosphate buffer saline (PBS), and the PBS was taken at every hour using a total substitution method. Thereafter, through the measurement of absorbance using a spectroscopic analysis method, the concentration of released drug was calculated to identify the release behavior.

Also, the organic-inorganic composite granules produced in each of Examples 1 to 4 were placed on a transwell, and cells were attached to the surface of a well plate to be cultured together in a culture medium. In order to quantify the degree of proliferation of cells, quercetin-sensitive organic-inorganic composite granules were removed and the culture medium was also removed. After performing washing with the PBS, a culture medium containing an MTS analysis liquid was applied and placed in a cell culture incubator for 2 hours. Thereafter, the culture medium was taken and measured for absorbance at 495 nm using a plater reader to analyze the cell proliferation tendency.

Referring to FIG. 2A, it can be confirmed that the drug was slowly released over time, and referring to FIG. 2C, it can be confirmed that the degree of cell proliferation was increased by the released drug. Accordingly, it can be seen that the organic-inorganic composite granules of the present invention may actually be used for drug delivery, and more specifically, may be used for treating osteoporosis and the like in a body.

Experimental Example 4

Identification of Drug Sustained Release Properties Through Cell Culture Properties In order to identify the cell culture properties of the organic-inorganic composite granules of the present invention, an experiment was conducted as follows.

The organic-inorganic composite granules containing quercetin at each concentration which were prepared in each of Examples 1 to 4 of the present invention were delivered using a transwell, and using a method for analyzing the cell proliferation and bone differentiation behavior for the quercetin released from the composite granules, osteoblasts (MC3T3) were cultured. Through the Cell Lysis method, the degree of bone differentiation of the cultured cells was confirmed as its representative factor, ALP activity, and DNA quantification was also performed. The results are shown in FIG. 3A and FIG. 3B, respectively.

Referring to FIG. 3, in the first week, the cell proliferation was almost the same, but in the second week, the cell proliferation occurred more when the quercetin content was greater, thereby confirming the sustained release properties of the organic-inorganic composite granules according to the present invention.

Experimental Example 5

Identification of Cell Supporting of Organic-Inorganic Granules

An organic-inorganic composite solution was prepared in the same manner as described in Example 5, and osteoblasts (MC3T3) were introduced into the composite solution at a concentration of $1.0 \times 10^6$ cells/ml and $5.0 \times 10^6$ cells/ml, and then stirred slowly. Thereafter, spraying was performed in the same manner as described in Example 5, and the mixture was dropped to a $CaCl_2$ solution to prepare organic-inorganic composite granules on a hydrogel phase. Thereafter, in order to confirm whether the cells were supported in the composite granules, dying was performed using a DAPI solution capable of identifying cell nuclei and confirmed through a fluorescence microscope. The result is shown in in FIG. 4. Referring to FIG. 4, it can be confirmed that the cells are uniformly supported in the organic-inorganic composite granules of the present invention.

Experimental Example 6

Identification of Uniform Dispersion According to Mixing Methods

In the mixing of the organic member and the inorganic member, in order to identify the degree of uniform dispersion of the organic-inorganic composite solution according to a mixing method, an experiment was conducted as follows.

An organic-inorganic composite solution was prepared in the same manner as described in Example 5. The prepared organic-inorganic composite solution was mixed for 6 minutes and 21 minutes using a magnetic stirrer, and at the same time, the prepared organic-inorganic composite solution was mixed for 6 minute using a rotation and revolution mixer. Thereafter, stirring was performed using an ultrasonic mixer for 15 minutes, and then dying was performed using an Alizarin red solution. The results were confirmed through an optical microscope. The results are shown in Table 5 below.

Referring to FIG. 5A, it can be seen that when stirring was performed using a general magnetic stirrer, the organic member and the inorganic member were not sufficiently mixed, and the inorganic member was heavily aggregated with each other. Also, it can be seen that when the stirring was performed using the general magnetic stirrer, the aggregation phenomenon was getting worse over time. However, referring to FIG. 5B, when mixing was performed using the rotation and revolution mixer and the ultrasonic mixer, the organic member and the inorganic member were uniformity mixed, so that the inorganic member was uniformity dispersed on the organic member.

Experimental Example 7

Identification of Composite Granule Size

In order to identify the size and size distribution of the organic-inorganic composite granules produced according to the present invention, an experiment was conducted as follows.

The form of granules was confirmed through an optical microscope for the organic-inorganic composite granules produced in each of Example 5 to Example 16, and the size and size distribution each thereof was confirmed using the ImageJ software. The results are shown in FIGS. 6A and 6B.

Referring to FIGS. 6A and 6B, the organic-inorganic composite granules according to the present invention are in a spherical shape, have a size in the range of about 200-500 μm, and have a size distribution not deviating from ±15%, thereby having a uniform size.

Among granules, ceramic granules were produced as follows, and the results were confirmed through experiments.

Example 17

Preparing Apatite Composite Liquid

A sample of an organic-inorganic composite liquid having a controlled content ratio of alginate, an organic particle, and nano-apatite, an inorganic particle, was prepared. The content ratio was set to 1:0 (Alg) and the sample was named with reference to a relative ratio of nano-apatite.

Producing Granules Using Micro-Granule Coater

Each of the organic-inorganic composite liquids prepared above was injected into a micro-granule coater to produce organic-inorganic granules. In the Example, B-395 pro manufactured by Buchi, a micro-granule coater using an electrostatic charge method, was used. Each composite liquid sample was sprayed through a nozzle of the micro-granule coater and dropped into a solution containing a polymerization-inducing material, and a polymerization reaction occurred in the solution to produce spherical organic-inorganic composite granules.

Stabilizing and Washing of Granules

A process for the stabilizing the organic-inorganic granules produced through the above process was performed, and washing and drying were performed on unreacted particles. The stabilizing and washing were performed using a phosphate buffer saline (PBS).

Producing Ceramic Granules Through Sintering Process

The organic-inorganic granules subjected to the previous process were sintered. Particularly, since organic particles were limited to alginate in the present embodiment, the temperature range for the sintering process was 1000-1300° C., and more specifically, the sintering process was performed at 1200° C.

Example 18

An apatite composite liquid was prepared by having an alginate as an organic particle and a nano-apatite as an inorganic particle at the content ratio thereof 1:0.1 (Alg_HA0.1). Ceramic granules were produced by performing the same process as in <Example 17> except for the content ratio of alginate and the nano-apatite.

Example 19

An apatite composite liquid was prepared by having an alginate as an organic particle and a nano-apatite as an inorganic particle at the content ratio thereof 1:0.25 (Alg_HA0.25). Ceramic granules were produced by performing the same process as in <Example 17> except for the content ratio of alginate and the nano-apatite.

Example 20

An apatite composite liquid was prepared by having an alginate as an organic particle and a nano-apatite as an inorganic particle at the content ratio thereof 1:1 (Alg_HA1). Ceramic granules were produced by performing the same process as in <Example 17> except for the content ratio of alginate and the nano-apatite.

Example 21

An apatite composite liquid was prepared by having an alginate as an organic particle and a nano-apatite as an inorganic particle at the content ratio thereof 1:2.5 (Alg_HA2.5). Ceramic granules were produced by performing the same process as in <Example 17> except for the content ratio of alginate and the nano-apatite.

Example 22

An apatite composite liquid was prepared by having an alginate as an organic particle and a nano-apatite as an inorganic particle at the content ratio thereof 1:5 (Alg_HA5). Ceramic granules were produced by performing the same process as in <Example 17> except for the content ratio of alginate and the nano-apatite.

Example 23

An apatite composite liquid was prepared by having an alginate as an organic particle and a nano-apatite as an inorganic particle at the content ratio thereof 1:7 (Alg_HA7). Ceramic granules were produced by performing the same process as in <Example 17> except for the content ratio of alginate and the nano-apatite.

Example 24

An apatite composite liquid was prepared by having an alginate as an organic particle and a nano-apatite as an inorganic particle at the content ratio thereof 1:9 (Alg_HA9). Ceramic granules were produced by performing the same process as in <Example 17> except for the content ratio of alginate and the nano-apatite.

Example 25

An apatite composite liquid was prepared by having an alginate as an organic particle and a nano-apatite as an inorganic particle at the content ratio thereof 1:10 (Alg_HA10). Ceramic granules were produced by performing the same process as in <Example 17> except for the content ratio of alginate and the nano-apatite.

Example 26

An apatite composite liquid was prepared by having an alginate as an organic particle and a nano-apatite as an inorganic particle at the content ratio thereof 1:4 (Alg_HA4). Ceramic granules were produced by performing the same process as in <Example 17> except for the content ratio of alginate and the nano-apatite.

Example 27

An apatite composite liquid was prepared by having an alginate as an organic particle and a nano-apatite as an inorganic particle at the content ratio thereof 1:6 (Alg_HA6). Ceramic granules were produced by performing the same process as in <Example 17> except for the content ratio of alginate and the nano-apatite.

Example 28

An apatite composite liquid was prepared by having an alginate as an organic particle and a nano-apatite as an inorganic particle at the content ratio thereof 1:8 (Alg_HA8). Ceramic granules were produced by performing the same process as in <Example 17> except for the content ratio of alginate and the nano-apatite.

Experimental Example 8> Comparison of Composite Liquids Having with Different Alginate:Apatite Ratios In <Experimental Example 8>, in order to identify the supporting limit of an inorganic matter and to compare the characteristics of granules accordingly, some samples of the organic-inorganic composite liquids of <Example 17> to <Example 25> having different content ratios of alginate, which is an organic particle, and nano-apatite (hydroxy apatite: HA), which is an inorganic particle, were compared to each other. [Table 2] represents the theoretical mass ratio and the actual mass ratio of an organic-inorganic composite liquid in which the ratio of alginate:nano-apatite was set to 1:0 to 1:10. Referring to [Table 2], it can be confirmed that the theoretical mass ratio and the actual mass ratio were improved as the relative content of the nano-apatite was increased. Particularly, it can be confirmed that the theoretical mass ratio was consistent with the content ratio of the alginate and the nano-apatite, while the actual mass ratio exhibited a different result from the corresponding ratio.

TABLE 2

| Sample | Alginate:Hydroxy-apatite | Theoretical weight ratio | Actual weight ratio |
|---|---|---|---|
| Alg | 1:0 | 0 | 0 |
| Alg_HA0.1 | 1:0.1 | 0.1 | 0.124 |
| Alg_HA0.25 | 1:0.25 | 0.25 | 0.271 |
| Alg_HA1 | 1:1 | 1 | 0.962 |
| Alg_HA2.5 | 1:2.5 | 2.5 | 2.796 |
| Alg_HA10 | 1:10 | 10 | 7.760 |

<Experimental Example 9> Identification of Crystal Formation in High Content Nano-Apatite Samples FIG. 9 is a drawing for identifying the crystal formation of <Example 25>. FIG. 9 represents an organic-inorganic composite liquid of an Alg HA10 sample in which alginate and nano-apatite were mixed at a content ratio 1:10, and referring to FIG. 9, it can be confirmed that spherical granules having a very uniform size were formed.

<Experimental Example 10> Change in Granule Size According to Inorganic Matter Content In <Experimental Example 10>, the effect of the content of the inorganic matter included in the organic-inorganic composite liquid prepared in Step a) on the size of granules produced through Steps b) to e) was examined. The sintering of Step e) was performed for 3 hours at 1200° C. to remove alginate, and the result confirmed in <Experimental Example 10> are summarized in [Table 3] below.

TABLE 3

| | Alg:HA | After cross-linking (mm) | After sintering (mm) | Remained size | Shrinkage |
|---|---|---|---|---|---|
| Alg | 1:0 | 2.32 | 0 | — | |
| Alg_HA0.1 | 1:0.1 | 2.36 | 0.49 | 21% | 79% |
| Alg_HA0.25 | 1:0.25 | 2.33 | 0.56 | 24% | 76% |
| Alg_HA1 | 1:1 | 2.34 | 0.76 | 32% | 68% |
| Alg_HA2.5 | 1:2.5 | 2.34 | 0.98 | 42% | 58% |
| Alg_HA10 | 1:10 | 2.25 | 1.4 | 62% | 38% |

The contents described in [Table 3] will be further described with reference to FIG. 10 and FIG. 13. FIG. 10 represents organic-inorganic composite granules produced through Step b) to Step d), and FIG. 11 represents ceramic granules produced through Step e) after Step b). In FIG. 10 and FIG. 11, (a) represents a sample of Alg, (b) represents a sample of Alg_HA0.1, (c) represents a sample of Alg_HA0.25, (d) represents a sample of Alg_HA1, (e) represents a sample of Alg_HA2.5, and (f) represent a sample of Alg_HA10.

Referring to after cross-linking (mm) tab of [Table 3] and FIG. 10, it can be confirmed that the organic-inorganic composite granules produced through polymerization induction after setting process conditions such as pressure, voltage, and frequency of the micro-granule coater equally were similarly formed having a size of 2.25-2.36 mm regardless of the relative content ratio of the inorganic matter.

On the other hand, referring to after cross-linking (mm) tab of [Table 3] and FIG. 11, it can be confirmed that the shape and size of the granules are formed differently according to the content ratio of the inorganic matter included in the first Step a). Particularly, in <Experimental Example 10>, it can be confirmed that as the content ratio of nano-apatite was increased, the size of the ceramic granules produced through the sintering process was increased, and the shrinkage rate was decreased. That is, it can be confirmed that in the case of the sample of Alg_HA0.1 of (b), shrinkage of about 80% was in progress while in the case of the sample of Alg HA10 of (f), shrinkage of about 40%, which is close to half of the shrinkage of the sample of (b) was in progress.

FIG. 12 and FIG. 13 represent a Field Emission Scanning Electron Microscope (FE-SEM) image of the ceramic granules produced after Step e) (S9). FIG. 12 and FIG. 13 also denote each sample shown in [Table 3] as (a) to (f). Referring to [Table 3] and FIG. 12, it can be seen that the ceramic granules produced by sintering the organic-inorganic granules which were produced according to each content ratio through Step e) had a different particle size and porosity after the sintering according to the ratio of the mixed inorganic matter. Particularly, as the content ratio of the nano-apatite was changed, it can be confirmed that the size and porosity of the ceramic particles after the sintering were changed.

Meanwhile, referring to [Table 3] and FIG. 13, it can be confirmed that the ceramic granules produced by sintering the organic-inorganic granules which were produced according to the content ratio of the inorganic matter included in Step a) had a changed crystal phase and surface roughness. Specifically, referring to (a), it can be seen that the granules composed of alginate alone, which is an organic matter, remained with sintered granules. Also, it can be confirmed that crystals forming the granules form a flat plate shape. The result is calcium oxide contained in a calcium chloride solution, which is a polymerization derivative used for the polymerization of alginate, and some identified needle-shaped crystals are thought to be apatite formed by calcium during the storage of the granules in the PBS solution in Step d).

Also, referring to (b) to (f), it can be confirmed that as the relative content ratio of the nano-apatite was increased, crystals in a wide plate shape were reduced but crystals in a needle shape were increased. Particularly, referring to (d) to (f), it can be confirmed that when the content ratio of the nano-apatite was 1.0 or greater, small particles were formed, and spherical particles were identified. The particles are thought to be mixed nano-apatite particles.

Through the results of <Experimental Example 10> described above, it can be confirmed that the content ratio of the inorganic matter included in Step a) may be a major variable affecting the size of the ceramic granules produced after sintering through Step e), and it can be confirmed that a user may produce ceramic granules having a diameter of a desired size based on accumulated data.

<Experimental Example 11> Energy Dispersive X-Ray (EDX) Analysis of Sintered Ceramic Granules FIGS. 14A and 14B and FIG. 15 show results of confirming components of crystals by each portion through an energy dispersive X-ray (EDX) analysis of the sintered ceramic granules. FIG. 14A and FIG. 15B show results for samples having a relative content ratio of nano-apatite of 0 to 0.25. Referring to FIG. 14A, it can be confirmed that crystals identified inside spectrum3 have a needle-shaped structure. Also, through the graph below, it can be confirmed that Ca/P, which is an atomic % (atomic concentration) ratio of Ca and P, is 1.66. This is similar to the Ca/P value of 1.67, which is the atomic % ratio of Ca and P shown in a typical apatite, and thus, the crystals may be thought to be crystals of apatite.

Referring to FIG. 14B, it can be confirmed that crystals identified inside spectrum2 have a plate-shaped structure. Also, through the graph below, it can be confirmed that the atomic % of P is close to 0. Through the result, it is assumed that the plate-shaped structure is calcium oxide formed by polymerization.

Meanwhile, FIG. 15 shows results of EDX detection of a portion seen in most samples having a relative content ratio of apatite of 1 to 10. In the corresponding portion, it was confirmed that the range of Ca/P, which is the atomic % ratio of Ca and P, was 1.54 to 1.72, and thus, it is thought that nano-apatite and tricalcium phosphate (TCP) used for the production are mixed with each other. In order to confirm the above, X-ray diffractometry (XRD) measurement was performed.

<Experimental Example 12> X-Ray Diffractometry (XRD) Measurement

FIG. 16 shows the XRD measurement result for a sample. Referring to FIG. 16, it can be confirmed that the ceramic granules containing alginate, which is an organic particle, in the organic-inorganic composite solution includes calcium oxide and apatite. As the relative content ratio of the nano-apatite included in the preparation of the composite liquid was increased from 0.1 to 10, it was confirmed that the content of the apatite identified in the crystals of the sintered sample was increased, whereas the content of the calcium oxide identified in the crystals was reduced.

Particularly, in the case of the Alg HA10 sample having a relative content ratio of nano-apatite of 10, almost no calcium oxide was detected in the granules after the sintering, and the granules were mostly composed of apatite. On the other hand, in the case of the Alg sample having a relative content ratio of nano-apatite of 0, no apatite component was detected in the granules after the sintering.

<Experimental Example 13> Comparison of Results According to Nano-Apatite Content In <Experimental Example 13>, ceramic granules were produced by controlling the process conditions of the microgranule coater. The preset process conditions were a frequency of 310 Hz, a pressure of 186-191 mBar, and a voltage of 1500 V, and a nozzle having a diameter of 200 μm was used. FIG. 17 shows the result of <Experimental Example 13>.

(a) is an Alg_HA1 sample, and represents granules produced through an organic-inorganic composite liquid in which alginate and nano-apatite are mixed at a content ratio of 1:1. (b) is an Alg_HA10 sample, and represents granules produced through an organic-inorganic composite liquid in which alginate and nano-apatite are mixed at a content ratio of 1:10. Comparing (a) and (b), it can be confirmed that the average size of the granules produced is confirmed to be 400-600 μm. That is, it can be seen that the relative content ratio of the nano-apatite contained in the organic-inorganic composite liquid in Step a) did not greatly affected the size of the granules before sintering.

Meanwhile, (c) is an Alg_HA1 sample, and represents ceramic granules produced by sintering the sample of (a). Also, (d) is an Alg_HA10 sample, and represents ceramic granules prepared by sintering the sample of (b). Comparing (c) and (d), the granules of (c) were shrunk to about 75% of the granules of (a), so that it can be confirmed that granules having a diameter of 100-150 μm were formed. On the other hand, the granules of (d) were shrunk to about 50% of the granules of (b), so that it can be confirmed that ceramic granules having a diameter of 200-300 μm were formed. Through the comparison of (c) and (d), it can be seen that the content ratio of alginate and nano apatite in the organic-inorganic composite liquid prepared in Step a) affects the diameter of the ceramic granules produced after the sintering, and it can be confirmed that when the relative content ratio of nano-apatite is high, shrinkage rate tends to decrease.

<Experimental Example 14> Comparison of Results According to Nano-Apatite Content 2

In <Experimental Example 14>, ceramic granules were produced by controlling the process conditions of the microgranule coater different from those of <Experimental Example 13>. The preset process conditions were a frequency of 1900 Hz, a pressure of 340-370 mBar, and a voltage of 1500 V, and a nozzle having a diameter of 200 μm was used. FIG. 18 shows the size comparison by ratio of alginate and nano-apatite of the granules produced under the conditions of <Experimental Example 14>.

(a) is an Alg_HA5 sample, and represents granules produced from an organic-inorganic composite liquid in which alginate and nano-apatite are mixed at a content ratio of 1:5. (b) is an Alg_HA7 sample, and represents granules produced from an organic-inorganic composite liquid in which alginate and nano-apatite are mixed at a content ratio of 1:7. (c) is an Alg_HA9 sample, and represents granules produced from an organic-inorganic composite liquid in which alginate and nano-apatite are mixed at a content ratio of 1:9. (d) is an Alg_HA10 sample, and represents granules produced through an organic-inorganic composite liquid in which alginate and nano-apatite are mixed at a content ratio of 1:10.

Referring to (a) to (d), it can be confirmed that granules having a uniform size were formed. Accordingly, through the method for producing ceramic granules according to an embodiment of the present invention, a plurality of granules having a similar size may be easily produced.

Meanwhile, FIG. 19 shows ceramic granules produced by sintering each sample illustrated in FIG. 19. Referring to (a) to (d) of FIG. 19, it can be confirmed that as the relative content ratio of the nano-apatite was increased, the size of the ceramic granules produced after the sintering was increased. Particularly, in the case of the Alg_HA5 sample of (b), the size was shrunk to about 92% from 347±57 μm before the sintering to 320±42 μm after the sintering, and in the case of the Alg_HA10 sample of (d), the size was shrunk to about 97% from 480±100 μm before the sintering to 466±50 μm after the sintering. The results represent the same aspect as the results of [Table 3] and FIG. 11. Based on the above, it can be confirmed that by adjusting the relative content ratio of the nano-apatite contained in the organic-inorganic composite liquid, it is possible to control the size of the ceramic granules after the sintering.

<Experimental Example 15> Comparison of Results According to Nano-Apatite Content 3

In <Experimental Example 15>, the size of ceramic granules after the sintering was compared when the relative content ratio of the nano-apatite was controlled using a 150 μm nozzle. The content ratio of alginate and nano-apatite was set to be 1:5 to 1:10. FIG. 20 is a graph showing the results of <Experimental Example 15>. Referring to FIG. 20, even when the 150 μm nozzle was used, it can be seen that as the relative content ratio of the nano-apatite was increased, the shrinkage rate was decreased, so that the size of the ceramic granules produced after the sintering was increased.

When alginate and nano-apatite were included at a content ratio of 1:5, the average size of the ceramic granules was 83±12 μm. Meanwhile, when alginate and nano-apatite were included at a content ratio of 1:10, the average size of the ceramic granules was 132±15 μm.

<Experimental Example 16> Comparison of Results According to Nano-Apatite Content 4

In <Experimental Example 16>, ceramic granules were produced using a 150 μm nozzle, and the size and shape of the ceramic granules according to the relative content ratio of nano-apatite were shown in a field emission scanning electron microscope (FE-SEM) image. FIG. 21 and FIG. 22 shows the result of <Experimental Example 16>.

FIG. 21 is an FE-SEM image for identifying the size of ceramic granules by content ratio of nano-apatite. (a) is an Alg_HA5 sample, (b) is an Alg_HA7 sample, (c) is an Alg_HA9 sample, and (d) is an Alg HA10 sample magnified by 500 times. Referring to (a) and (b), it can be confirmed that even when the content ratio of the nano-apatite was different, the ceramic granules maintained a shape closed to a spherical shape.

Meanwhile, FIG. 22 is an image of each sample of FIG. 21 magnified by 10000 times. Referring to (a) to (d), it can be confirmed that a sample having a high ratio of alginate formed a large number of interparticle pores. In summary, based on the results of FIG. 22, it can be confirmed that porosity may be controlled according to the relative content ratio of the nano-apatite.

<Experimental Example 17> Comparing Ceramic Granules According to Process Conditions In <Experimental Example 17>, the characteristics of ceramic granules after sintering were compared according to the nozzle size and the relative content of the nano-apatite. FIG. 23A, 23B, 23C and FIGS. 24A and 24B show the results of <Experimental Example 17>.

FIG. 23A and FIG. 23B show the size of ceramic granules according to the relative content ratio of the nano-apatite of the ceramic granules produced using 200 μm and 150 μm nozzles, respectively. Referring to FIG. 23A and FIG. 23B, it can be confirmed that as the relative content ratio of the nano-apatite was increased, the size of the ceramic granules was increased. The result represent the same aspect that, as described above, as the content ratio of the nano-apatite included in Step a) was increased, the shrinkage rate of the ceramic granules produced after the sintering was decreased.

FIG. 23C is a graph for comparing FIG. 23A and FIG. 23B. Referring to FIG. 23C, it can be confirmed that the ceramic granules produced using a 200 μm nozzle had a smaller size than the ceramic granules produced using a 150 μm nozzle. Though the above, it was confirmed that the size of the sintered ceramic granules were increased by increasing the size of the nozzle and the relative content ratio of nano-apatite.

Meanwhile, FIG. 24A and FIG. 24B shows the composition of ceramic granules according to the relative content ratio of the nano-apatite of the ceramic granules produced using 200 μm and 150 μm nozzles, respectively. In both graphs, a graph located at the top represents a sample including the nano-apatite at a high content, and a graph located at the bottom represents the Alg sample, then Alg_HA5, Alg_HA7, Alg_HA9, and Alg_HA10 samples.

Particularly, referring FIG. 24A and FIG. 24B, in a portion in which the content ratio of the alginate and the nano-apatite was 1:5 to 1:10 in both the 150 μm nozzle of FIG. 24A and the 150 μm nozzle of FIG. 24B, no significant change was observed in the crystal phase according to the relative content ratio of the nano-apatite. That is, it can be seen that the composition change according to a nozzle size was not confirmed. Through the above, it can be confirmed that in the corresponding area, it is possible to control only the size of the granules according to the size of a nozzle and the relative content ratio of the nano-apatite and that there was no significant effect on the composition.

FIG. 25A and FIG. 25D show the size and size distribution of ceramic granules according to the relative content ratio of the nano-apatite of the ceramic granules produced using a 120 μm nozzle. To this end, the diameter of 200 ceramic granules was measured through an optical program.

Referring to FIG. 25A to FIG. 25D, it was confirmed that as the relative content ratio of the nano-apatite was increased, the size of the sintered ceramic granules was increased. When the content ratio of alginate, which is an organic matter, and nano-apatite, which is an inorganic particle, was 1:4, the size of the ceramic particle was measured to be 60.8±8.4 μm, and when the content ratio of alginate, which is an organic matter, and nano-apatite, which is an inorganic particle, was 1:6, 1:8, and 1:10, the size of the ceramic particles were measured to be 73.2±10.4 μm, 82.3±10.9 μm and 88.6±12.2 μm, respectively.

FIG. 26A and FIG. 26D show the size and size distribution of ceramic granules according to the relative content ratio of the nano-apatite of the ceramic granules produced using a 150 μm nozzle. To this end, the diameter of 200 ceramic granules was measured through an optical program.

Referring to FIG. 26A to FIG. 26D, it was confirmed that as the relative content ratio of the nano-apatite was increased, the size of the sintered ceramic granules was increased, which is similar to the results of the FIG. 25A to FIG. 25D. When the content ratio of alginate, which is an organic matter, and nano-apatite, which is an inorganic particle, was 1:4, the size of the ceramic particle was measured to be 79.3±10.2 μm, and when the content ratio of alginate, which is an organic matter, and nano-apatite, which is an inorganic particle, was 1:6, 1:8, and 1:10, the size of the ceramic particles were measured to be 89.4±13.0 μm, 107.1±14.2 μm, and 123.3±17.1 μm, respectively.

FIG. 27A and FIG. 27D show the size and size distribution of ceramic granules according to the relative content ratio of the nano-apatite of the ceramic granules produced using a 200 μm nozzle. To this end, the diameter of 200 ceramic granules was measured through an optical program.

Referring to FIG. 27A to FIG. 27D, it was confirmed that as the relative content ratio of the nano-apatite was increased, the size of the sintered ceramic granules was increased, which is similar to the results of the FIG. 25A to FIG. 25D and FIG. 26A to FIG. 26D. When the content ratio of alginate, which is an organic matter, and nano-apatite, which is an inorganic particle, was 1:4, the size of the ceramic particle was measured to be 104.3±14.7 μm, and when the content ratio of alginate, which is an organic matter, and nano-apatite, which is an inorganic particle, was 1:6, 1:8, and 1:10, the size of the ceramic particles were measured to be 118.8±16.3 m, 146.1±22.8 μm, and 159.1±22.7 μm, respectively.

FIG. 28A and FIG. 28C show the particle size distribution of ceramic granules according to change in the ratio of alginate and nano-apatite using the results of FIGS. 25A to 27D above based on the nozzle size.

Referring to FIG. 28A to FIG. 28C, a particle size distribution of 60.8-88.6 μm was obtained according to the relative content ratio of the nano-apatite of ceramic granules produced using the 120 m nozzle, and it can be seen that as the relative content ratio of the nano-apatite was increased, the average diameter of the ceramic granules was increased. Also, a particle size distribution of 79.3-123.3 μm was obtained according to the relative content ratio of the nano-apatite of ceramic granules produced using the 150 m nozzle, and it can be seen that as the relative content ratio of the nano-apatite was increased, the average diameter of the ceramic granules was increased. Also, a particle size distribution of 104.0-159.1 μm was obtained according to the relative content ratio of nano-apatite of ceramic granules produced using the 200 μm nozzle, and it can be seen that as the relative content ratio of the nano-apatite was increased, the average diameter of the ceramic granules was increased.

Also, in the method of preparing ceramic granules, since the relative content ratio of nano-apatite to an organic matter was increased from 1:4 to 1:10, the standard deviation was increased from 0.59 to 0.86 for the 120 μm nozzle, from 0.72 to 1.21 for the 150 μm nozzles, and 1.04 to 1.60 for the 20 μm. Through the above, in the method of preparing ceramic granules, it can be seen that as the relative content ratio of the nano-apatite to the organic matter is increased, the distribution of the size of the ceramic granules was increased.

FIG. 29A to FIG. 29D show the particle size distribution of ceramic granules according to change in the nozzle size based on the ratio of alginate and nano-apatite using the results of FIGS. 25A to 27D above based on the ratio of alginate and nano-apatite.

Referring to FIG. 29A to FIG. 29D, it can be seen that the ceramic granules produced under the condition of the ratio of alginate and nano apatite of 1:4 had the average diameter thereof increased from 60.8 μm to 104.0 μm as the size of the nozzle was increased from 120 μm to 200 μm. Also, it was confirmed that the ceramic granules produced under the condition of the ratio of alginate and nano apatite of 1:6 had the average diameter thereof increased from 73.2 μm to 118.8 μm as the size of the nozzle was increased from 120 μm to 200 μm, and it was confirmed that the ceramic granules produced under the condition of the ratio of alginate and nano apatite of 1:8 had the average diameter thereof increased from 82.3 μm to 146.1 μm as the size of the nozzle was increased from 120 μm to 200 μm. It was also confirmed that the ceramic granules produced under the condition of the ratio of alginate and nano apatite of 1:10 had the average diameter thereof increased from 88.6 μm to 159.1 μm as the size of the nozzle was increased from 120 μm to 200 μm.

Also, in the production method of ceramic granules, the ceramic granules produced under the condition of the ratio of alginate and nano apatite of 1:4 had the standard deviation for the average diameter increased from 0.59 to 1.04, as the size of the nozzle was increased from 120 μm to 200 μm, and in the production method of ceramic granules, when the ratio of a and nano-apatite is 1:6. 1:8, and 1:10, the standard deviation value was increased from 0.74 to 1.04, from 0.77 to 1.61, and from 0.86 to 1.60, respectively, as the size of the nozzle was increased from 120 μm to 200 μm. Through the above, it was confirmed that as the size of the nozzle was increased, the diameter and standard deviation of the ceramic granules prepared was increased thereby.

As the relative content ratio of nano-apatite to an organic matter was increased from 1:4 to 1:10, the standard deviation was increased from 0.59 to 0.86 for the 120 μm nozzle, from 0.72 to 1.21 for the 150 μm nozzles, and 1.04 to 1.60 for the 200 μm nozzle. Through the above, in the method of preparing ceramic granules, it can be seen that as the relative content ratio of the nano-apatite to the organic matter is increased, the distribution of the size of the ceramic granules was increased.

<Experimental Example 18> Identification of Uniform Dispersion According to Mixing Methods In the mixing of the organic member and the inorganic member, in order to identify the degree of uniform dispersion of the organic-inorganic composite solution according to a mixing method, an experiment was conducted as follows. The organic-inorganic composite solution prepared in Example 18 was mixed for 6 minutes and 21 minutes using a magnetic stirrer, and at the same time, the prepared organic-inorganic composite solution was mixed for 6 minute using a rotation and revolution mixer. Thereafter, stirring was performed using an ultrasonic mixer for 15 minutes. The results are shown in FIG. 30A and FIG. 30B.

Referring to FIG. 30A and FIG. 30B, it can be seen that when stirring was performed using a general magnetic stirrer, the organic member and the inorganic member were not sufficiently mixed, and the inorganic member was heavily aggregated with each other. Also, it can be seen that when the stirring was performed using the general magnetic stirrer, the aggregation phenomenon was getting worse over time. However, when mixing was performed using the rotation and revolution mixer and the ultrasonic mixer, the organic member and the inorganic member were uniformity mixed, so that the inorganic member was uniformity dispersed on the organic member.

Although the present invention has been described in detail through exemplary embodiments above, those skilled in the art will understand that various modifications are possible within the scope of the present invention without departing from the scope of the present invention. Therefore, the scope of the present invention should not be limited to the embodiments described above, but should be determined by all modifications or variations derived not only from the following claims but also from the claims and the equivalent concepts thereof.

The invention claimed is:

1. A method for manufacturing granules, the method comprising:
preparing an organic member solution;
uniformly dispersing an inorganic member in the organic member solution at a weight ratio of 1 to 10 based on an organic member to form an organic-inorganic composite solution, the uniformly dispersing including,
dispersing the inorganic member with a rotation and revolution mixer to form an organic-inorganic composite solution, and
stirring the organic-inorganic composite solution with an ultrasonic mixer;

spraying the organic-inorganic composite solution in an electrostatic charge manner after the uniformly dispersing; and polymerizing the organic member contained in the sprayed organic-inorganic composite solution to form granules having a hydrogel phase, wherein an average diameter of the granules is between 100 to 2000 μm, and each diameter of the granules falls in a range of −20% to +20% to the average size of granules, wherein the organic member comprises at least one organic matter among alginate, collagen, gelatin, chitosan, cellulose, and hyaluronate, wherein the inorganic member comprises at least one among hydroxy apatite (HA), dicalcium phosphate (DCP), tricalcium phosphate (TCP), tetracalcium phosphate (TTCP), and octacalcium phosphate (OCP).

2. The method of claim 1, wherein the weight ratio of the inorganic member dispersed in the organic member solution to the organic member is 5 to 10.

3. The method of claim 1, wherein the polymerizing is performed by dropping the sprayed organic-inorganic composite solution to a polymerization-inducing solution.

4. The method of claim 1, wherein the inorganic member comprises a functional member.

5. The method of claim 1, further comprising:
supporting a functional member or cells in the organic-inorganic composite solution.

6. The method of claim 1, wherein a concentration of the organic member solution is 0.5-5 wt %.

7. The method of claim 1, wherein a size of the inorganic member is 20 nm to 10 μm.

8. The method of claim 1, wherein the dispersing is performed in a range where a temperature of the organic-inorganic composite solution does not exceed 40° C.

9. The method of claim 1, wherein the spraying the organic-inorganic composite solution in an electrostatic charge manner is performed by using a micro-granule coater, and the micro-granule coater has a spray nozzle size in a range of 50-1,000 μm, a voltage in a range of 500-2,500 V, a pressure in a range of 100-1,500 mbar, and a vibration frequency in a range of 100-6,000 Hz.

10. The method of claim 1, wherein the formed hydrogel phase does not comprise a dispersant.

11. The method of claim 1, further comprising:
washing and drying the formed hydrogel phase; and
sintering the washed and dried hydrogel phase.

12. The method of claim 9, wherein the average diameter of the granules is controlled according to change in the spray nozzle size, pneumatic condition and frequency of the micro-granule coater.

13. The method of claim 1, the polymerizing is performed by any one among ion crosslinking, chemical crosslinking, and photo crosslinking.

14. The method of claim 13, wherein the ion crosslinking uses at least one polymerization-inducing material among calcium chloride ($CaCl_2$), calcium sulfate ($CaSO_4$), and calcium carbonate ($CaCO_3$).

15. The method of claim 11, wherein the sintering is performed at a temperature range of 1000-1300° C. to remove the organic member.

16. The method of claim 11, wherein a size and porosity of the granules are controlled according to content of the inorganic member to the organic member.

17. The method of claim 11, wherein the manufactured granules are granulated particles comprising calcium oxide (CaO) and content of the calcium oxide is 1 to 10 mass %.

* * * * *